(12) United States Patent
Tass et al.

(10) Patent No.: US 12,193,988 B2
(45) Date of Patent: *Jan. 14, 2025

(54) APPARATUS AND METHOD FOR TREATING A PATIENT USING VIBRATION STIMULI, TACTILE STIMULI AND/OR THERMAL STIMULI

(71) Applicant: GRETAP AG, Zug (DE)

(72) Inventors: Peter Alexander Tass, Munich (DE); Laetitia Mayor, Marly (CH); Jean-Christophe Roulet, Lignieres/Ne (CH); Urban Schnell, Muenchenbuchsee/Be (CH)

(73) Assignee: GRETAP AG, Zug (CH)

( * ) Notice: Subject to any disclaimer, the term of this patent is extended or adjusted under 35 U.S.C. 154(b) by 201 days.

This patent is subject to a terminal disclaimer.

(21) Appl. No.: 17/674,522

(22) Filed: Feb. 17, 2022

(65) Prior Publication Data

US 2022/0168180 A1 Jun. 2, 2022

Related U.S. Application Data

(63) Continuation of application No. 16/453,590, filed on Jun. 26, 2019, now Pat. No. 11,253,424, which is a (Continued)

(30) Foreign Application Priority Data

Feb. 11, 2010 (DE) .......................... 102010000390.5

(51) Int. Cl.
*A61H 23/00* (2006.01)
*A61F 7/00* (2006.01)
(Continued)

(52) U.S. Cl.
CPC .......... *A61H 23/0245* (2013.01); *A61F 7/00* (2013.01); *A61H 7/001* (2013.01);
(Continued)

(58) Field of Classification Search
CPC ................ A61H 23/00; A61H 2201/02; A61H 2201/0207; A61H 2201/0221;
(Continued)

(56) References Cited

U.S. PATENT DOCUMENTS 2,924,216 A * 2/1960 Stewart .............. A61H 23/0263
601/60
4,370,602 A 1/1983 Jones
(Continued)

FOREIGN PATENT DOCUMENTS

CA 2623464 A1 10/2009
CN 2172112 Y 7/1994
(Continued)

OTHER PUBLICATIONS

Benninghoff, et al., Der funktionelle Bau der Teile, Lehrbuch der Anatomie des Menschen. Dargestellt unter Bevorzugung funktioneller Zusammenhange. 3. Bd. Nervensystem, Haut and Sinnesorgane, [Textbook of Human Anatomy, Presented With Emphasis on Functional Relationships, 3rd vol. Nervous System, Skin and Sensory Organs] pp. 126-137, Urban and Schwarzenberg, Munich 1964. (w/concise explanation).
(Continued)

*Primary Examiner* — Tu A Vo
(74) *Attorney, Agent, or Firm* — ArentFox Schiff LLP

(57) ABSTRACT

A device and method are provided for treating a patient with vibration and/or tactile and/or thermal stimuli. The device includes first and second stimulating units for generating first and second stimuli respectively. The stimuli are vibration and/or tactile and/or thermal stimuli, and each of the
(Continued)

stimuli is repeated on average at a frequency of 1 to 60 Hz. The stimuli are generated partly at different times.

11 Claims, 21 Drawing Sheets

Related U.S. Application Data continuation of application No. 13/578,375, filed as application No. PCT/DE2011/075004 on Jan. 18, 2011, now abandoned.

(51) Int. Cl.
*A61H 7/00* (2006.01)
*A61H 23/02* (2006.01)

(52) U.S. Cl.
CPC ..... *A61H 23/0254* (2013.01); *A61H 2201/02* (2013.01); *A61H 2201/10* (2013.01); *A61H 2201/1418* (2013.01); *A61H 2201/1669* (2013.01); *A61H 2201/5002* (2013.01); *A61H 2201/5084* (2013.01); *A61H 2205/06* (2013.01); *A61H 2205/065* (2013.01); *A61H 2205/10* (2013.01); *A61H 2205/12* (2013.01); *A61H 2230/10* (2013.01); *A61H 2230/30* (2013.01); *A61H 2230/40* (2013.01); *A61H 2230/60* (2013.01); *A61H 2230/65* (2013.01)

(58) Field of Classification Search
CPC .... A61H 2201/0228; A61H 2201/0242; A61H 2201/12; A61H 2201/1207; A61H 2201/1215; A61H 2201/165; A61H 2201/1657; A61H 2201/1659; A61H 2201/1661; A61H 2201/1666; A61H 2201/1669; A61H 2201/1671; A61H 2201/1673; A61H 2201/1676; A61H 2201/1678; A61H 2201/50; A61H 2201/5002; A61H 2201/5005; A61H 2201/5007; A61H 2201/501; A61H 2201/5023; A61H 23/02; A61H 23/006; A61H 23/004; A61H 23/0245; A61H 23/0263; A61H 2023/002; A61F 7/00–123; A61F 2007/0001–126

See application file for complete search history.

(56) References Cited

U.S. PATENT DOCUMENTS

| | | | |
|---|---|---|---|
| 5,336,159 | A | 8/1994 | Cheng |
| 5,611,771 | A | 3/1997 | Taylor |
| 5,746,702 | A | 5/1998 | Gelfgat et al. |
| 5,800,481 | A | 9/1998 | Loos |
| 6,217,533 | B1 * | 4/2001 | McCambridge ... A61H 23/0263 601/56 |
| 6,432,072 | B1 * | 8/2002 | Harris ............... A61H 23/0254 601/111 |
| 6,458,089 | B1 * | 10/2002 | Ziv-Av ............... A61B 5/1101 600/595 |
| 6,934,580 | B1 * | 8/2005 | Osorio ............... A61B 5/4094 607/45 |
| 7,347,833 | B2 * | 3/2008 | Kim .................. A61H 15/0078 601/103 |
| 7,917,221 | B2 | 3/2011 | Tass |
| 8,423,144 | B2 | 4/2013 | Tass |
| 10,548,810 | B2 * | 2/2020 | Stanbridge ............ A61H 7/003 |
| 2004/0097841 | A1 | 5/2004 | Savellev et al. |
| 2005/0024025 | A1 | 2/2005 | Sevenhans |
| 2006/0100567 | A1 | 5/2006 | Marchitto et al. |
| 2007/0232962 | A1 | 4/2007 | Zumeris et al. |
| 2007/0100214 | A1 | 5/2007 | Steinert |
| 2007/0135860 | A1 * | 6/2007 | Tass ................... A61N 1/36082 607/45 |
| 2007/0167888 | A1 * | 7/2007 | Taylor ................. A61H 1/0292 601/84 |
| 2007/0203435 | A1 | 8/2007 | Novak |
| 2007/0255187 | A1 | 11/2007 | Branch |
| 2008/0200854 | A1 | 8/2008 | Hobson et al. |
| 2008/0275372 | A1 | 11/2008 | Shimotori |
| 2009/0005713 | A1 | 1/2009 | Podrazhansky |
| 2009/0036809 | A1 * | 2/2009 | Nishio ............... A61H 15/0078 601/134 |
| 2009/0187124 | A1 * | 7/2009 | Ludlow ................ A61H 23/00 601/47 |
| 2009/0221943 | A1 | 9/2009 | Burbank |
| 2009/0227914 | A1 * | 9/2009 | Kanaoka ............. A61H 9/0078 601/84 |
| 2010/0244504 | A1 | 9/2010 | Colja |
| 2010/0249637 | A1 | 9/2010 | Walter |
| 2010/0274175 | A1 * | 10/2010 | Bernabei ............ A61N 1/0412 604/20 |
| 2010/0318007 | A1 * | 12/2010 | O'Brien .............. A61H 23/004 601/48 |
| 2010/0324631 | A1 | 12/2010 | Tass |
| 2011/0201977 | A1 | 8/2011 | Tass |
| 2011/0288370 | A1 * | 11/2011 | Orten ................. A61H 23/0263 600/38 |
| 2012/0316624 | A1 * | 12/2012 | Smith .................. A61N 2/006 607/99 |
| 2013/0245713 | A1 | 9/2013 | Tass |

FOREIGN PATENT DOCUMENTS

| | | |
|---|---|---|
| CN | 2300412 Y | 12/1998 |
| CN | 2645656 Y | 10/2004 |
| CN | 101431940 A | 5/2009 |
| JP | H07-96016 A | 4/1995 |
| JP | 2003-293207 A | 10/2003 |
| JP | 2005-348766 A | 12/2005 |
| JP | 2007-268048 A | 10/2007 |
| JP | 2008523852 A * | 7/2008 |
| TW | 200714272 | 4/2007 |
| WO | 01/03638 A1 | 1/2001 |
| WO | 2009/136931 A1 | 11/2009 |

OTHER PUBLICATIONS

A.T. Winfree: "Phase Control of Neural Pacemakers"; Science, vol. 197, Aug. 19, 1977, pp. 761-763.
Rodger J. Elble et al.: "Phase Resetting and Frequency Entrainment of Essential Tremor"; Experimental Neurology, vol. 116, 1992, pp. 355-361.
Robert G. Lee, MD et al.; "Resetting of Tremor by Mechanical Perturbations: A Comparison of Essential Tremor and Parkinsonian Tremor"; Annals of Neurology, vol. 10, No. 6. Dec. 1981, pp. 523-531.
H. Teravainen et al.; "Effects of Kinesthetic Inputs on Parkinsonian Tremor"; Advances in Neurology, vol. 24, 1979, pp. 161-173.
N. Bathien et al.; "Inhibition and synchronisation of tremor induced by a muscle twitch"; Journal of Neurology, Neurosurgery and Psychiatry, vol. 43, 1980, pp. 713-718.
Peter A. Tass; "Desynchronization of brain rhythms with soft phase-resetting techniques"; Biological Cybernetics, vol. 87, 2002, pp. 102-115.
Peter A. Tass; "Phase Resetting Associated with Changes of Burst Shape"; Journal of Biological Physics, vol. 22, 1996, pp. 125-155.
Peter A. Tass; "Phase resetting in medicine and biology: Stochastic modeling and data analysis":, Chapter 2, pp. 11-54, Springer Verla , Berlin (1999).
Chinese Office Action issued for corresponding CH 2014012700950930, issuing date Jan. 30, 2014 (with English translation.

* cited by examiner

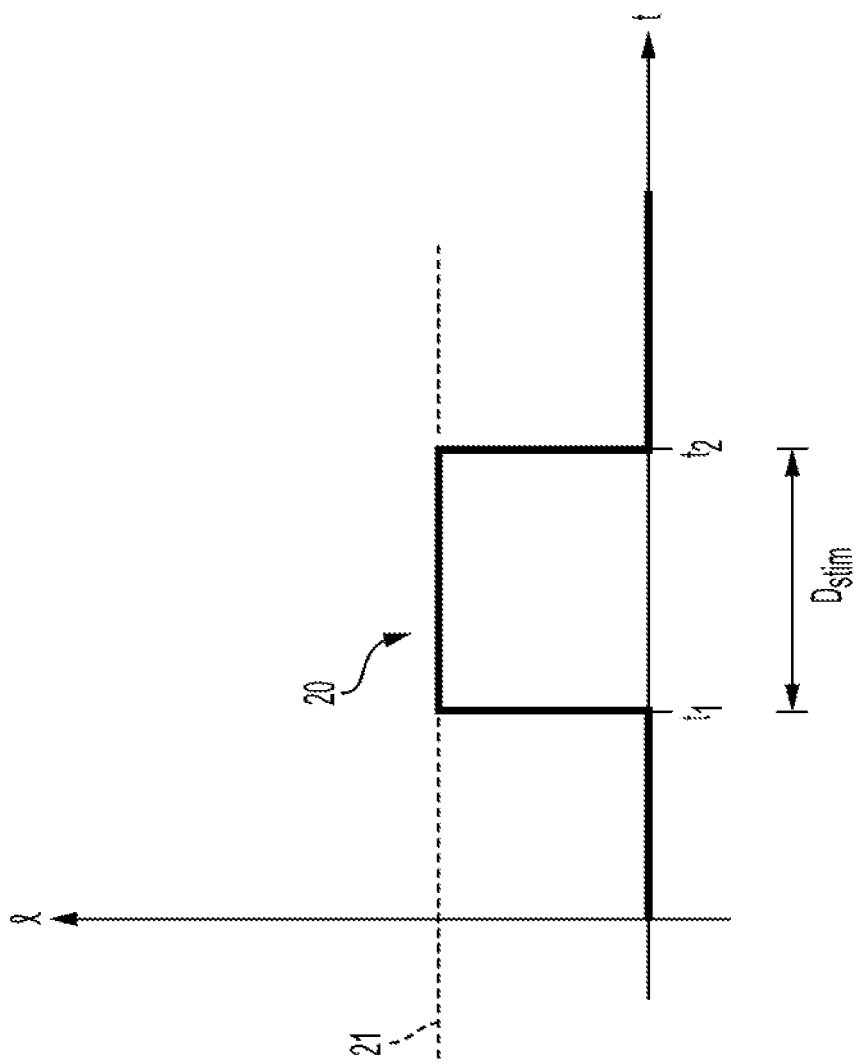

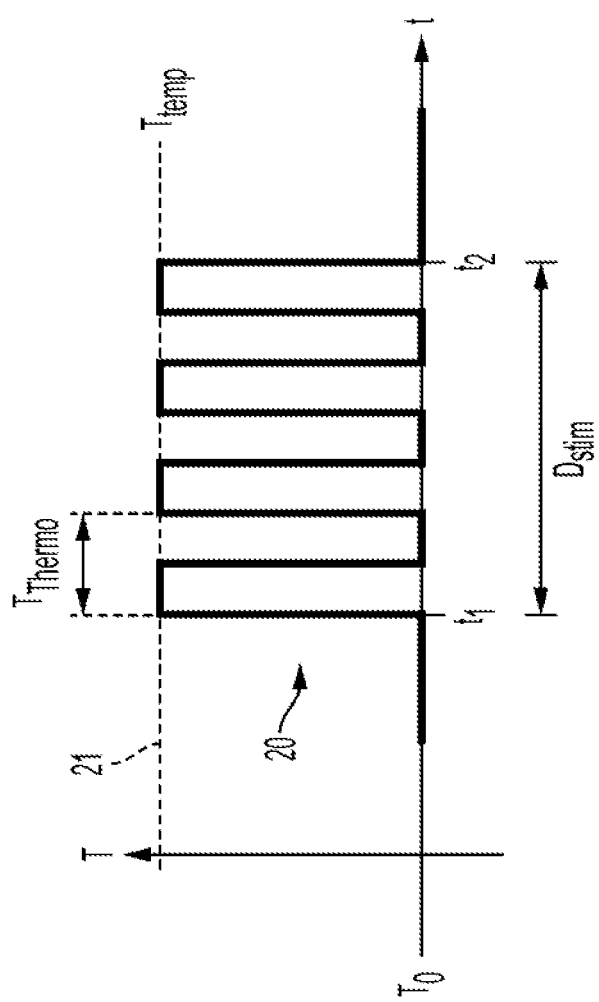

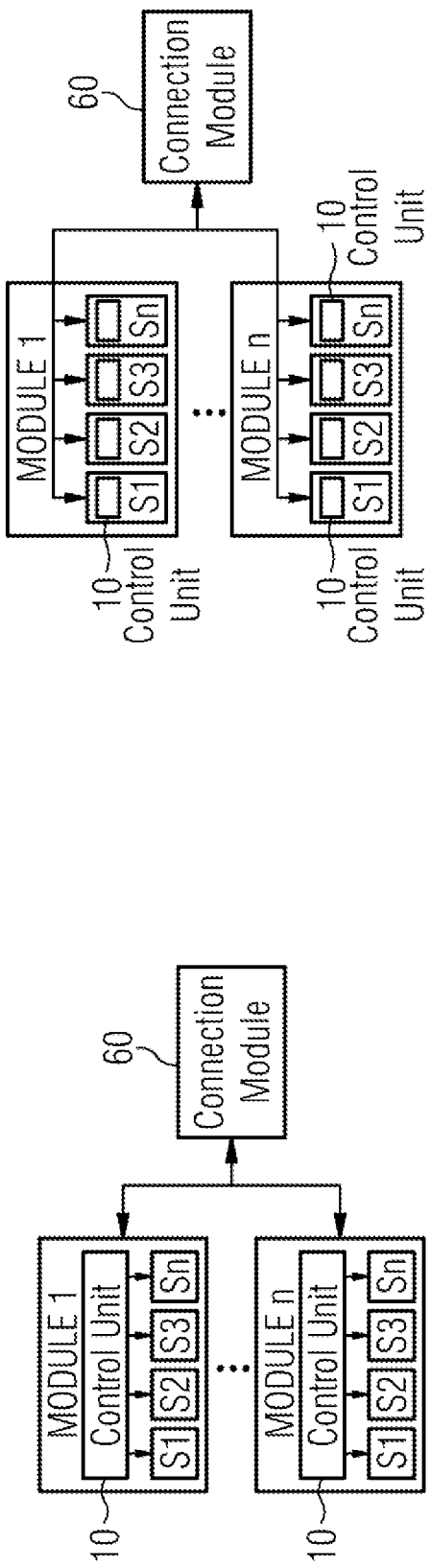
FIG. 19B
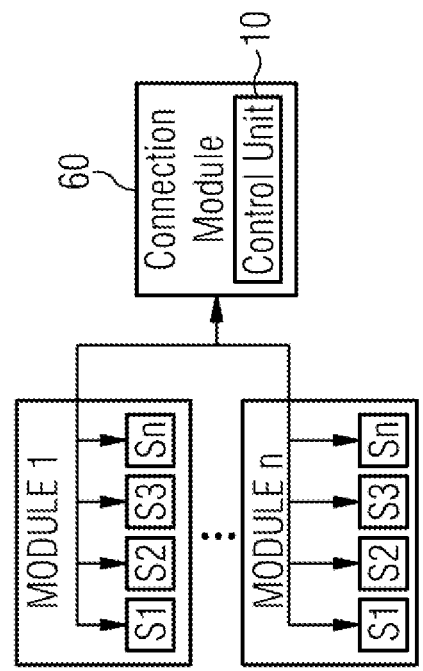
FIG. 19C
FIG. 19A

APPARATUS AND METHOD FOR TREATING A PATIENT USING VIBRATION STIMULI, TACTILE STIMULI AND/OR THERMAL STIMULI

CROSS REFERENCE TO RELATED APPLICATIONS

This application is a continuation of U.S. patent application Ser. No. 16/453,590, filed Jun. 26, 2019, which is a continuation of U.S. patent application Ser. No. 13/578,375, filed Oct. 22, 2012, now abandoned, which is National Stage entry of International Application No. PCT/DE2011/075004, filed on Jan. 18, 2011, which claims priority to German Application No. 10 2010 000 390.5, filed on Feb. 11, 2010, the contents of each of these priority applications are hereby incorporated by reference in their entirety.

TECHNICAL FIELD

The invention relates to an apparatus and to a method for treating a patient using vibration stimuli and/or tactile stimuli and/or thermal stimuli.

The invention in particular relates to a stimulation apparatus and to a stimulation method for treating diseases in which there is increased neuronal synchronization. In particular diseases of the brain can be treated using the invention such as locomotor disorders, Parkinson's disease, essential tremor, dystonia, migraine, tension headache, spasticity, functional disorders after stroke, neuropathic pain, chronic pain, neuralgias, post-amputation pain, tremor and other functional disorders following brain trauma. Gastrointestinal diseases such as irritable bowel syndrome can, however, also be treated. In this respect, painful cramps and inefficient bowel motility can be unlearned. The treatment using the apparatus in accordance with the invention can also have an antispasmodic and pain-relieving effect in cases of ulcerative colitis and of Crohn's disease. Furthermore, asthma bronchiale, cardiac ischemia and peripheral arterial occlusive disease can be treated using the apparatus in accordance with the invention.

BACKGROUND

The only therapies—if any—for treating the aforesaid diseases are pharmacological or stereotactic therapies. The effectiveness of pharmacological therapies is typically limited in time. The stereotactic treatment harbors relevant risks such as the risk of arterial bleeding on the implantation of brain pacemakers.

SUMMARY

Against this background, a method is provided for treating a patient with a disease in which there is an increased neuronal synchronization of neuron activity of the patient. In an exemplary aspect, the method includes generating, by a plurality of stimulation units, vibration stimuli for stimulating neurons in the patient to treat the disease by desynchronizing the neuron activity of the patient; controlling the plurality of stimulation units to generate each of the respective vibration stimuli in as a sequence of pulses with a vibration frequency $f_{vib}$; selecting the vibration frequency $f_{vib}$ based on pathological features experienced by the patient with the disease, the vibration frequency $f_{vib}$ for the sequence of pulses of each stimuli being selected in a range between 30 Hz and 300 Hz, wherein $f_{vib}=1/T_{vib}$ with $T_{vib}$ being a period of duration of the respective stimuli; controlling the plurality of stimulation units to generate the respective vibration stimuli in respective sequences with a time offset between two mutually following stimuli of an average of $1/(f_{stim} \times N)$, where $f_{stim}$ is a frequency in a range of 1 to 60 Hz and N is a number of the plurality of stimulation units; controlling each of the plurality of stimulation units to generate at most one of the stimuli during a repeating time period having a length of $T_{stim}$, wherein $f_{stim}=1/T_{stim}$; and varying an order in which the plurality of stimulation units generate the respective sequences of the stimuli for each time period of the length of $T_{stim}$.

BRIEF DESCRIPTION OF DRAWINGS

The invention will be described in more detail in an exemplary manner in the following with reference to an embodiment and to the drawings. There are shown in these:

FIGS. 5A to 5C illustrate schematic representations of thermal stimuli;

FIGS. 18 to 19C illustrate schematic representations of an apparatus 300 for generating vibration stimuli, tactile stimuli and/or thermal stimuli in accordance with a further embodiment.

DETAILED DESCRIPTION

Figure 1:
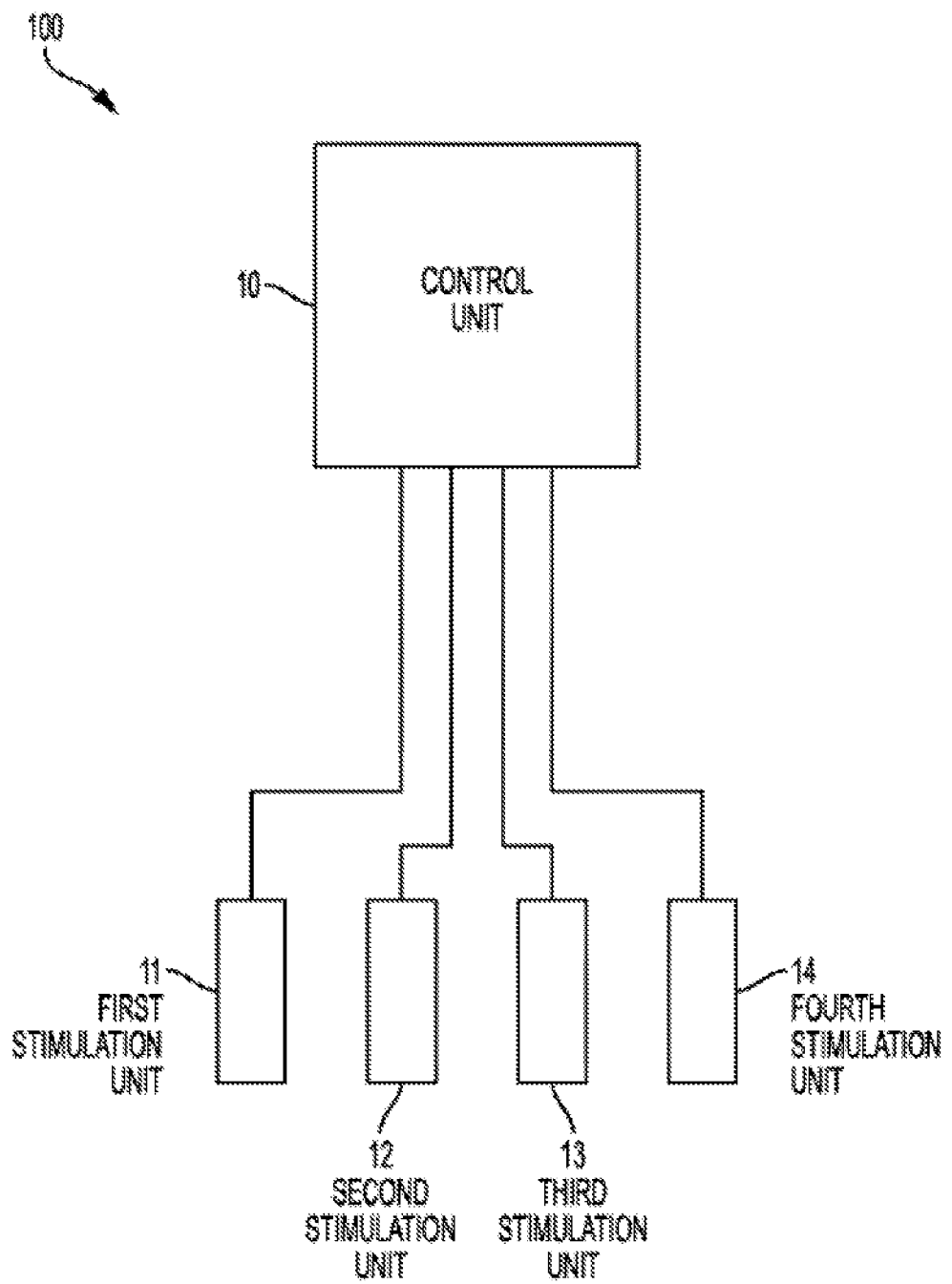
FIG. 1 illustrates a schematic representation of an apparatus 100 for generating vibration stimuli, tactile stimuli and/or thermal stimuli in accordance with an embodiment.

An apparatus 100 for the non-invasive treatment of a patient using vibration stimuli, tactile stimuli and/or thermal stimuli is shown schematically in FIG. 1. The apparatus 100 in the embodiment shown in FIG. 1 comprises a first stimulation unit 11 for generating first stimuli, a second stimulation unit 12 for generating second stimuli, a third stimulation unit 13 for generating third stimuli and a fourth stimulation unit 14 for generating fourth stimuli. The embodiment shown in FIG. 1 is only to be understood in an exemplary manner. Alternatively to this embodiment, the apparatus 100 can include any desired number N (N=2, 3, 4, 5, 6, 7, 8, 9, 10, 11, 12, . . . ) of stimulation units. The apparatus 100 can furthermore have a control unit 10 which is connected to the stimulation units 11 to 14 via suitable connection lines or via radio and which controls the generation of the stimuli. The control unit 10 can also be integrated in one or more or all the stimulation units 11 to 14.

The stimulation units 11 to 14 can each generate one or more stimuli from the group of vibration stimuli, tactile stimuli and thermal stimuli. The stimulation units 11 to 14 are designed such that they can be placed on the skin of the patient. Depending on the disease and/or on the effected parts of the body, the stimulation units 11 to 14 are secured on the skin of the patient in a suitable arrangement, for example to the arm, to the leg, to the hand and/or to the foot of the patient. Vibration stimulation, tactile stimulation and thermal stimulation can each be administered on the skin either individually or in combination depending on the symptoms.

The majority of stimulation units 11 to 14 allow different receptive areas of the skin to be stimulated with temporal and spatial coordination via the individual stimulation units 11 to 14. The stimulation units 11 to 14 can be arranged on the skin of the patient such that the stimuli applied to the skin tissue are forwarded via nerve conductors to different target regions which e.g. lie in the spinal cord and/or in the brain. Consequently, different target regions in the spinal cord and/or in the brain can be stimulated with possibly different and/or time-offset stimuli by means of the apparatus 100 during the same stimulation time period.

Figure 2:
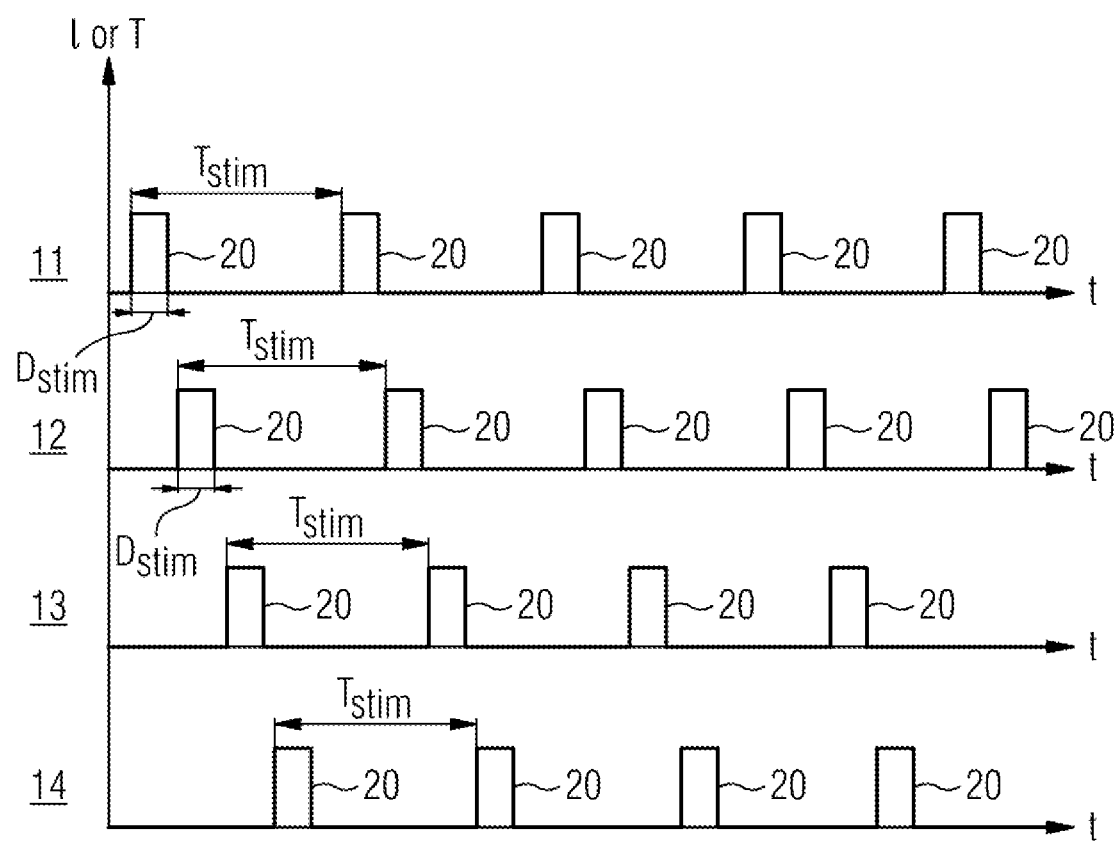
FIG. 2 illustrates a schematic representation of a stimulation method carried out using the apparatus 100.

A stimulation method which can be carried out using the apparatus 100 is shown schematically in FIG. 2. The stimuli 20 applied via the stimulation units 11 to 14 are shown over the time t in FIG. 2.

In the method shown in FIG. 2, each of the stimulation units 11 to 14 applies the stimulus 20 periodically to the respective receptive area of the skin on which the stimulation unit 11 to 14 is attached. The frequency $f_{stim}=1/T_{stim}$ ($T_{stim}$=period duration) at which the stimuli 20 generated by each of the stimulation units 11 to 14 are repeated can lie in the range from 1 to 60 Hz and in particular in the range from 30 to 60 Hz or in the range from 1 to 30 Hz or in the range from 1 to 20 Hz or in the range from 5 to 20 Hz, but can also adopt lower or higher values. The duration $D_{stim}$ of an individual stimulus 20 can in particular depend on the type of the stimulus. The ordinate shown in FIG. 2 likewise depends on the type of stimuli 20. With a vibration stimulus or a tactile stimulus, for example, the deflection 1 of a stimulation element can be entered over the time t; with a thermal stimulus a temperature T can be shown. The stimuli 20 applied via the different stimulation units 11 to 14 can be identical or different.

Different embodiments of individual vibration stimuli 20 are shown un FIGS. 3A, 3B, 3C and 3D. The deflection 1 of a stimulation element is entered against the time t there. The stimulation element is deflected from its position of rest at the time $t_1$ in FIG. 3A and is pressed into the skin of the patient. The position of the skin surface is shown by a dashed line 21. Once the stimulation element has come into contact with the skin, a periodic vibration stimulus is applied at a frequency $f_{vib}=1\ T_{vib}$ in the range from 30 to 300 Hz ($T_{vib}$=period duration of the vibration stimulus). At a frequency $f_{vib}$ of 300 Hz, the stimulation element can exert a force of approximately 2N. The duration $D_{stim}$ of the vibration stimulus 20 can lie in the range from 10 to 500 ms. The stimulation $$0 < D_{stim} < \frac{T_{stim}}{N}, \quad (1)$$

where N is the number of stimulation units. A range of 10 to 250 ms e.g. results for the stimulation duration $D_{stim}$ for $T_{stim}$=1Hz and N=4. Time-overlapping stimuli can, however, also be used.

Figure 3A:
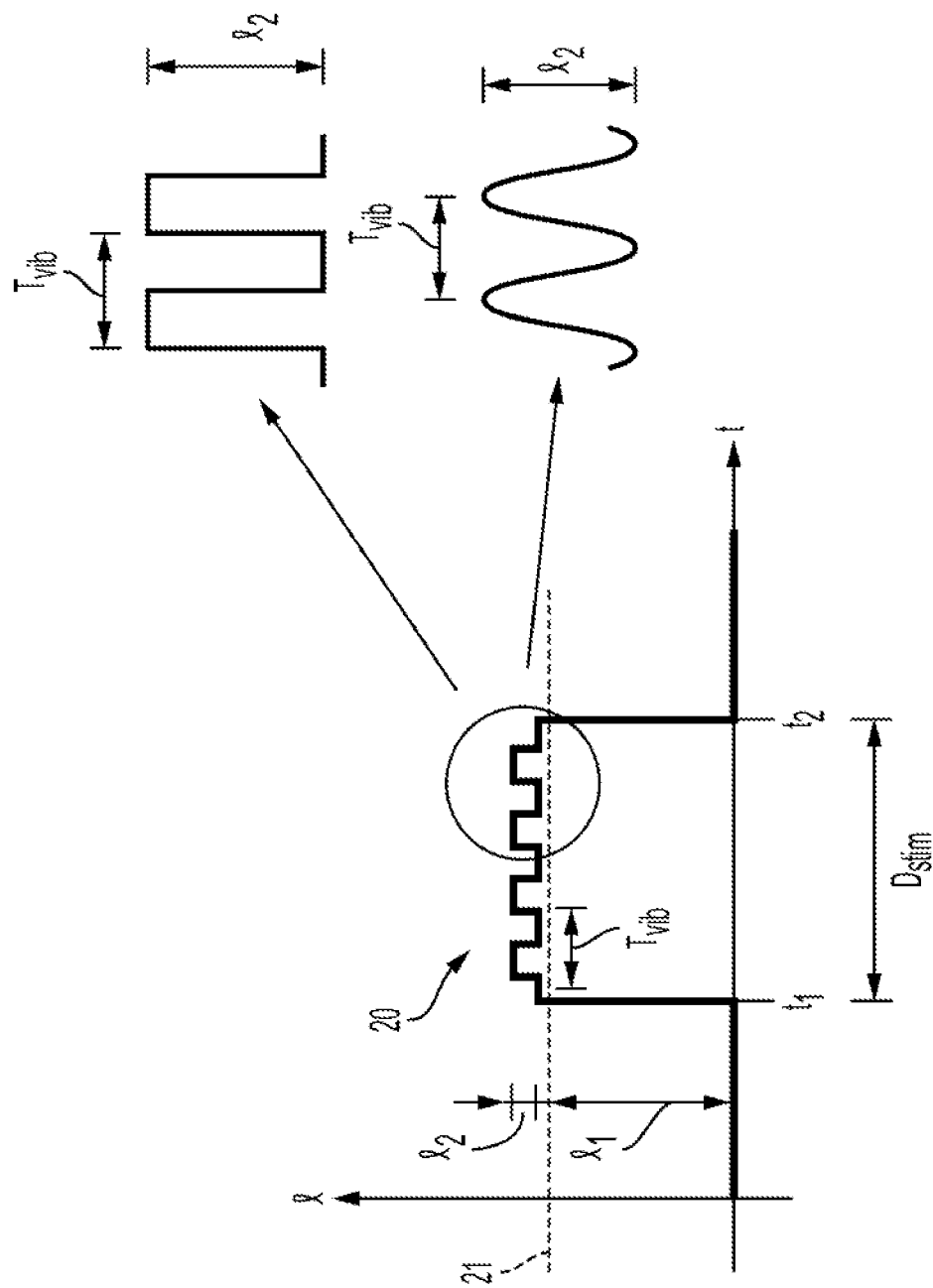
FIGS. 3A to 3D illustrate schematic representations of vibration stimuli.

At the time $t_2$, the stimulation element is again moved to its position of rest where it has no contact with the skin. As shown in FIG. 3A, the vibration stimulus 20 can be a rectangular or sinusoidal stimulus, but it can also have different forms. The deflection $1_1$ shown in FIG. 3A for pressing the stimulation element into the skin can lie in the range from 0.5 to 3 mm. The deflection $1_2$ of the stimulation element during the vibration can amount to between 0.1 and 0.5 mm.

Figure 3B:
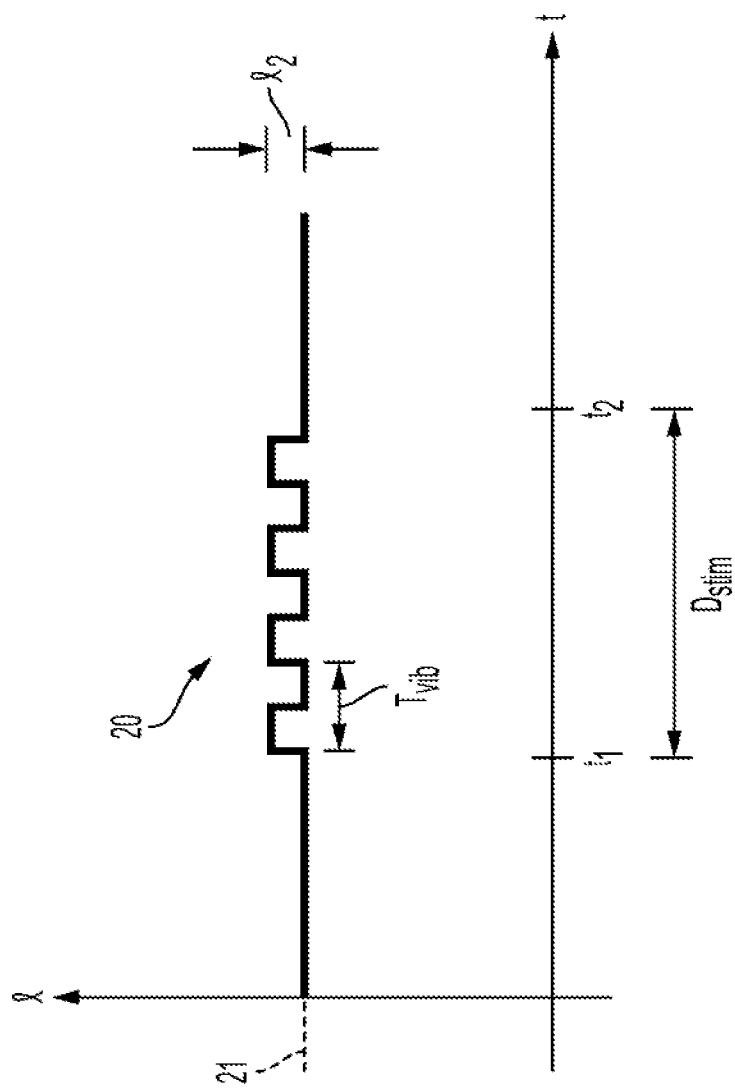

A variation of the vibration stimulus 20 shown in FIG. 3A is shown in FIG. 3B. In the embodiment shown in FIG. 3B, the stimulation element is always in contact with the skin of the patient. A vibration stimulus 20 as described above is applied during the stimulation period $D_{stim}$.

Figure 3C:
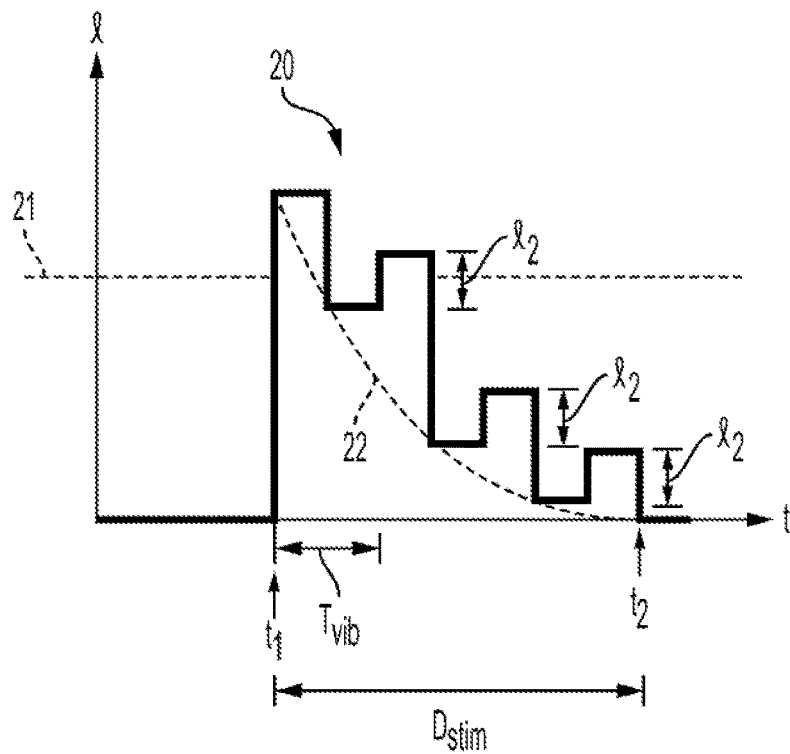

A further variation of the vibration stimulus 20 is shown in FIG. 3C. Unlike the vibration stimulus 20 of FIG. 3A, the stimulation element is already withdrawn during the stimulation period $D_{stim}$ so that the vibrations press less far into the skin as the time duration increases and the stimulation element is finally completely released from the skin. The withdrawal of the stimulation element can, for example, take place along a linear or non-linear curve 22, e.g. an exponential curve, on which the vibrations fib of the stimulation element are superimposed. In the example shown in FIG. 3C, the falling flank of each pulse extends down to the curve 22. The adjoining pulse has a fixedly preset height $1_2$, i.e. the rising flank of each pulse has the height $1_2$.

Figure 3D:
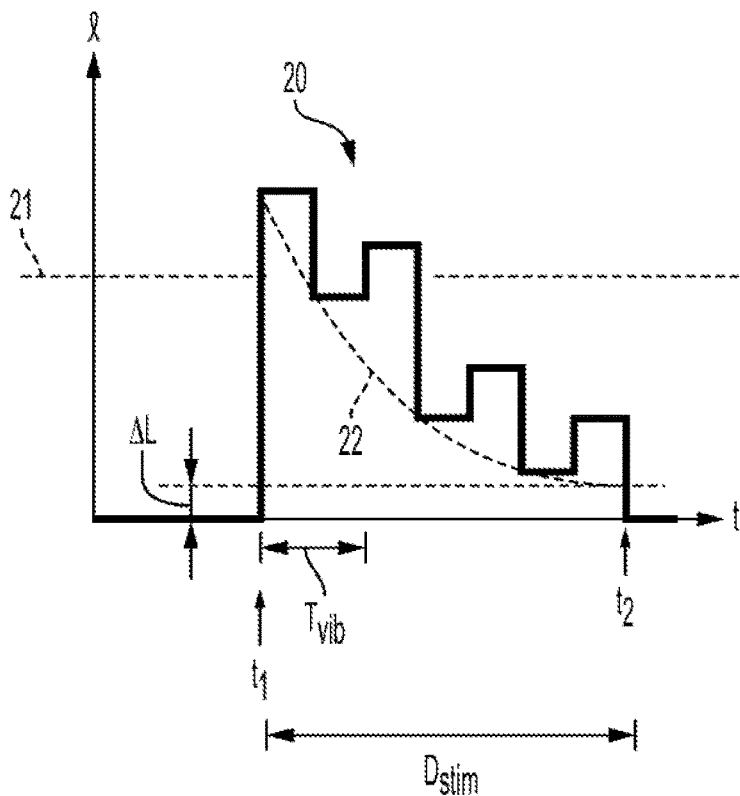

A variation of the vibration stimulus 20 of FIG. 3*c* is shown in FIG. 3D. The curve 22 there does not return to the zero line (1=0), but has a fixedly preset offset ΔL from the zero line.

Figure 4:
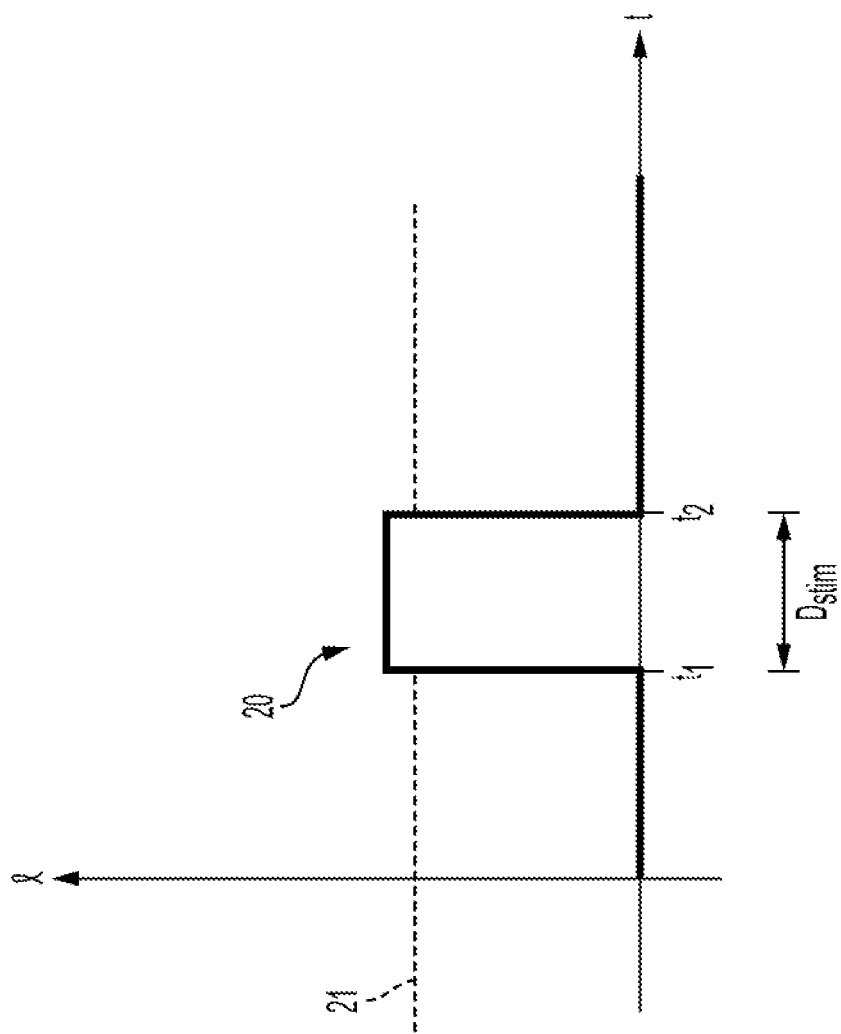
FIG. 4 illustrates a schematic representation of a tactile stimulus.

An embodiment of a tactile stimulus 20 is shown in FIG. 4. The stimulation element is pressed into the skin of the patent at the time $t_1$, remains there for the stimulation duration $D_{stim}$ and is withdrawn again at the time $t_2$. The stimulation duration $D_{stim}$ with a tactile stimulation 20 lies in the range from 10 to 500 ms. The stimulation duration $D_{stim}$ in particular lies in the range given above in (1); time-overlapping stimuli can, however, also be used.

Figure 5B:
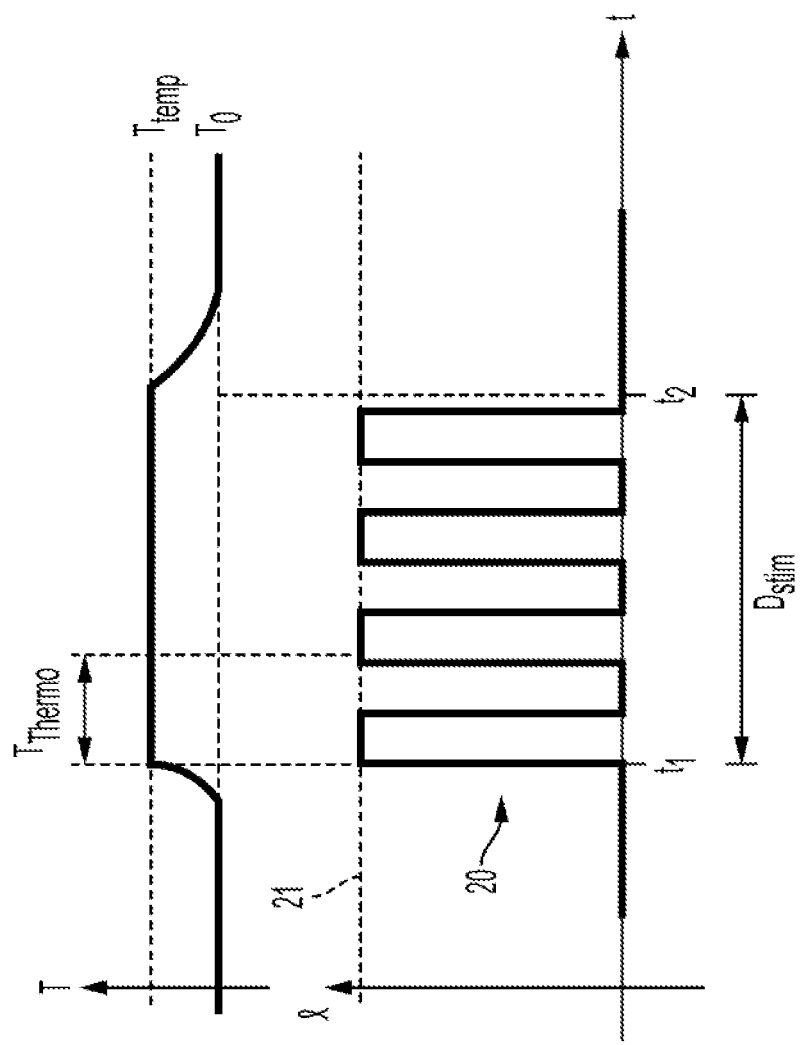

Different embodiments of individual thermal stimuli 20 are shown in FIGS. 5A, 5B and 5C. In the embodiments shown in FIGS. 5A and 5B, a stimulation element is heated or cooled to a temperature $T_{temp}$. As is shown in FIG. 5B, the temperature $T_{temp}$ can only be generated just before the application of the thermal stimulus 20. In this case, the stimulation element has a temperature To during the stimulation pauses which corresponds e.g. to the room temperature. Alternatively, the stimulation element can be maintained at a constant temperature $T_{temp}$.

In the embodiment in accordance with FIG. 5A, the heated or cooled stimulation element is applied to the skin of the patient at the time $t_1$ and remains there for the total stimulation duration $D_{stim}$. In contrast to this, in the embodiment in accordance with FIG. 5B, the stimulation element is applied periodically to the skin with a frequency $f_{thermo}$ during the stimulation duration Dstim and is removed again. The frequency $f_{thermo}=1/T_{thermo}$ can lie in the range from 1 to 10 Hz ($T_{thermo}$=period duration of the thermal stimulus).

The thermal stimulus 20 shown in FIG. 5C substantially corresponds to the thermal stimulus 20 of FIG. 5B. The difference is that the thermal stimulus 20 of FIG. 5C is generated contactlessly. Here, the stimulation temperature $T_{temp}$ is generated by electromagnetic radiation, for example by infrared light. Furthermore, the electromagnetic radiation is periodically varied with the frequency $f_{thermo}=1/T_{thermo}$ (e.g. by switching an infrared radiator on and off).

With thermal stimuli, the stimulation duration $D_{stim}$ lies in the range from 10 to 500 ms. The stimulation duration $D_{stim}$ in particular lies in the range given above in (1); time-overlapping stimuli can, however, also be used. The temperature $T_{temp}$ can be from 22 to 42° C. The temperature $T_0$ is as a rule the body temperature of the patient. The frequency $f_{thermo}$ can lie between 1 and 10 Hz, but can also lie outside this range.

It is also conceivable that an individual stimulus 20 includes a plurality of types of stimulus. For example, the vibration stimulus 20 shown in FIG. 3A can simultaneously be a thermal stimulus provided that the stimulation element exerting the stimulus is correspondingly heated or cooled. The vibration stimulus 20 of FIG. 3A is furthermore simultaneously a tactile stimulus (tactile receptors are activated by the impact of the stimulation element on the skin).

The apparatus 100 can in particular be used for treating diseases in which an increased neuronal synchronization is present. In particular diseases of the brain can be treated using the apparatus 100 such as locomotor disorders, Parkinson's disease, essential tremor, dystonia, migraine, tension headache, spasticity, functional disorders after stroke, neuropathic pain, chronic pain, neuralgias, post-amputation pain, tremor and other functional disorders following brain trauma. Gastrointestinal diseases such as irritable bowel syndrome can, however, also be treated. Furthermore ulcerative colitis, Crohn's disease, asthma bronchiale, cardiac ischemia and peripheral arterial occlusive disease can be treated using the apparatus 100.

The aforesaid diseases can be caused by a disorder of the bioelectric communication of neural assemblies which are connected in specific circuits. In this respect, a neuronal population continuously generates pathological neuronal activity and possibly a pathological connectivity associated therewith (network structure). In this respect, a large number of neurons synchronously form action potentials, i.e. the participating neurons fire excessively synchronously. In addition, there is the fact that the pathological neuronal population has an oscillatory neuronal activity, i.e. the neurons fire rhythmically. In the case of neurological or psychiatric diseases, the mean frequency of the pathological rhythmic activity of the affected neural assemblies lies approximately in the range from 1 to 30 Hz, but can also be outside this range. In healthy people, the neurons fire qualitatively differently, however, e.g. in an uncorrelated manner.

The stimuli applied by the stimulation units 11 to 14 are received by receptors disposed in or beneath the skin and are forwarded to the nervous system. These receptors include, for example, Merkel cells, Ruffini corpuscles, Meissner's corpuscles and hair follicle receptors which in particular act as receptors for the tactile stimuli 20. The vibration stimuli 20 are predominantly directed to proprioception. The vibration stimuli 20 can be received by receptors disposed in the skin, in the muscles, in the subcutaneous tissue and/or in the sinews of the patient. Pacini's corpuscles, which communicate vibration perceptions and accelerations, can be named as examples for the vibration stimuli. The thermal stimuli are received by the thermoreceptors of the skin. They are warm receptors (also called heat receptors, warm sensors or heat sensors) and cold sensors (also called cold receptors). The cold sensors are more superficial in the skin of people; the heat receptors somewhat lower.

The stimuli 20 generated by the stimulation elements 11 to 14 are designed such that they effect a reset of the phase of neuronal activity of the stimulated neurons in a neuronal population when they are received by the corresponding receptors and are conducted via the nerve conductors to the neuronal population in the brain or spinal cord with a pathologically synchronous and oscillatory activity. The phase of stimulated neurons is set to a specific phase value, e.g. to 0°, independently of the current phase value by the reset. The phase of the neuronal activity of the pathological neuronal population is thus controlled by means of a direct stimulation.

It is furthermore possible on the basis of the plurality of stimulation elements to stimulate the pathological neuronal populations at different points. The stimuli 20 applied to different points of the skin are namely forwarded to different points in the brain or spinal cord. This makes it possible to reset the phase of neuronal activity of the pathological neuronal population at the different stimulation points at different times. As a result, the pathological neuronal population whose neurons were previously active synchronously and at the same frequency and phase are split into a plurality of subpopulations. The neurons are still synchronous and also still fire at the same pathological frequency within a subpopulation, but each of the subpopulations has that phase with respect to its neuronal activity which is imposed on it by the stimulus.

Due to the pathological interaction between the neurons, the state with at least two subpopulations generated by the stimulation is unstable and the total neuronal population fast approaches a state of complete desynchronization in which the neurons fire without correlation. The desired state i.e. the complete desynchronization is thus not immediately present after the application of the stimuli 20, but is usually adopted within a few periods or even in less than one period of pathological activity.

With the above-described type of stimulation, the ultimately desired desynchronization is only made possible by the pathologically increased interaction between the neurons. In this respect, a self-organization process is utilized which is responsible for the pathological synchronization. The same process has the effect that a division of a total population into subpopulations with different phases is followed by a desynchronization. In contrast to this, no effective desynchronization would take place without pathologically increased interaction of the neurons.

Furthermore, a reorganization of the connectivity of the disturbed neuronal networks can be achieved by the stimulation using the apparatus 100 so that long-continuing therapeutic effects can be brought about.

Figure 6:
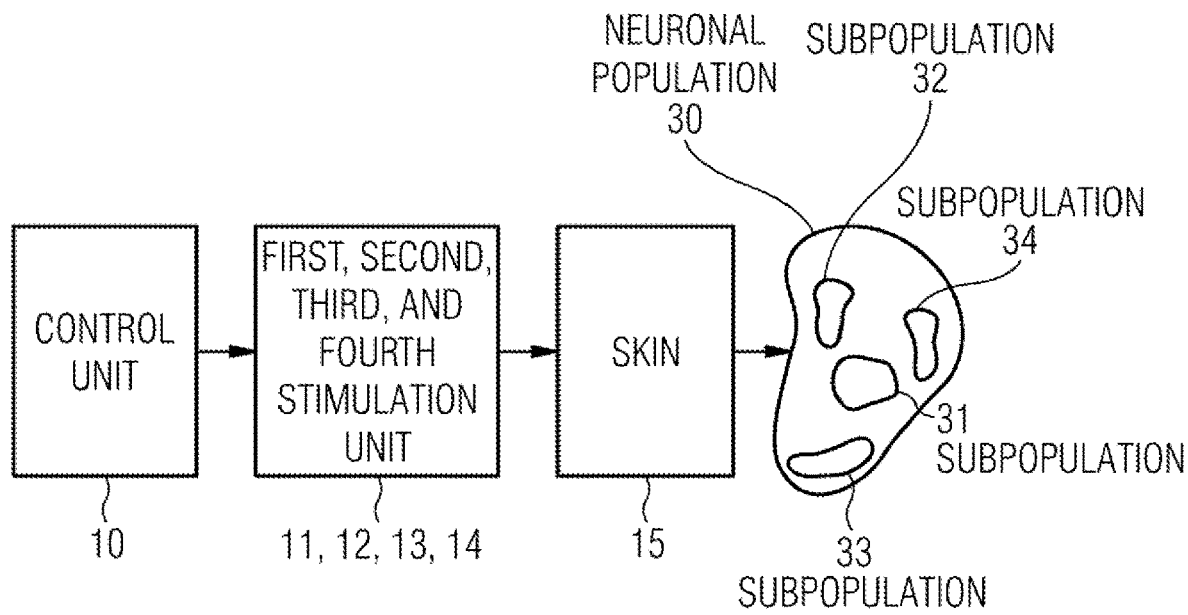
FIG. 6 illustrates a schematic representation of the apparatus 100 during its intended use.

The stimulation of a plurality of subpopulations of a pathologically active neuronal population 30 using the apparatus 100 is shown schematically in FIG. 6. The respective receptors are stimulated at different points of the skin 15 by vibration stimuli 20 and/or tactile stimuli 20 and/or thermal stimulation 20 via the stimulation units 11 to 14. The stimuli 20 applied by the stimulation units 11, 12, 13 and 14 are forwarded to different subpopulations 31, 32, 33 and 34 of the neuronal populations 30 (stimuli from stimulation unit 11 to subpopulation 31, stimuli from stimulation unit 12 to subpopulation 32, stimuli from stimulation unit 13 to subpopulation 33 and stimuli from stimulation unit 14 to subpopulation 34) and reset the phases of these subpopulations at respective different points in time, whereby a desynchronization of the total neuronal population 30 is achieved.

The achieved stimulation of specific regions of the brain or of the spinal cord is make possible by the somatotopic association of body regions with these regions. The stimulation units 11 to 14 can be applied, for example, to the foot, lower leg and thigh or to the hand, the lower arm and upper arm of the patient. Different neurons are stimulated by the stimuli applied to the respective points due to the somatotopic structure of the neural pathways. The somatotopic association of skin points with regions of the brain is described, for example, in A. Benninghoff et al.: "Lehrbuch der Anatomie des Menschen. Dargestellt unter Bevorzugung funktioneller Zusammenhänge. 3.Bd. Nervensystem, Haut und Sinnesorgane", [Textbook of Human Anatomy. Presented With Emphasis on Functional Relationships. 3rd Vol., Nervous System, Skin and Sensory Organs"], Urban und Schwarzenberg, Munich 1964.

Different procedures can be followed to achieve a desynchronization of the total neuronal population 30 by a time-offset reset of the phases of the subpopulations 31 to 34 of the pathologically synchronous neuronal population 30. For example, the stimuli 20 which effect a reset of the phase of neurons can be output to the respective receptive fields of the skin offset in time via the different stimulation units 11 to 14. Furthermore, the stimuli can e.g. be applied offset in phase or with different polarities so that they also lead as a result to a time-offset reset of the phases of the different subpopulations 31 to 34.

Figure 7:
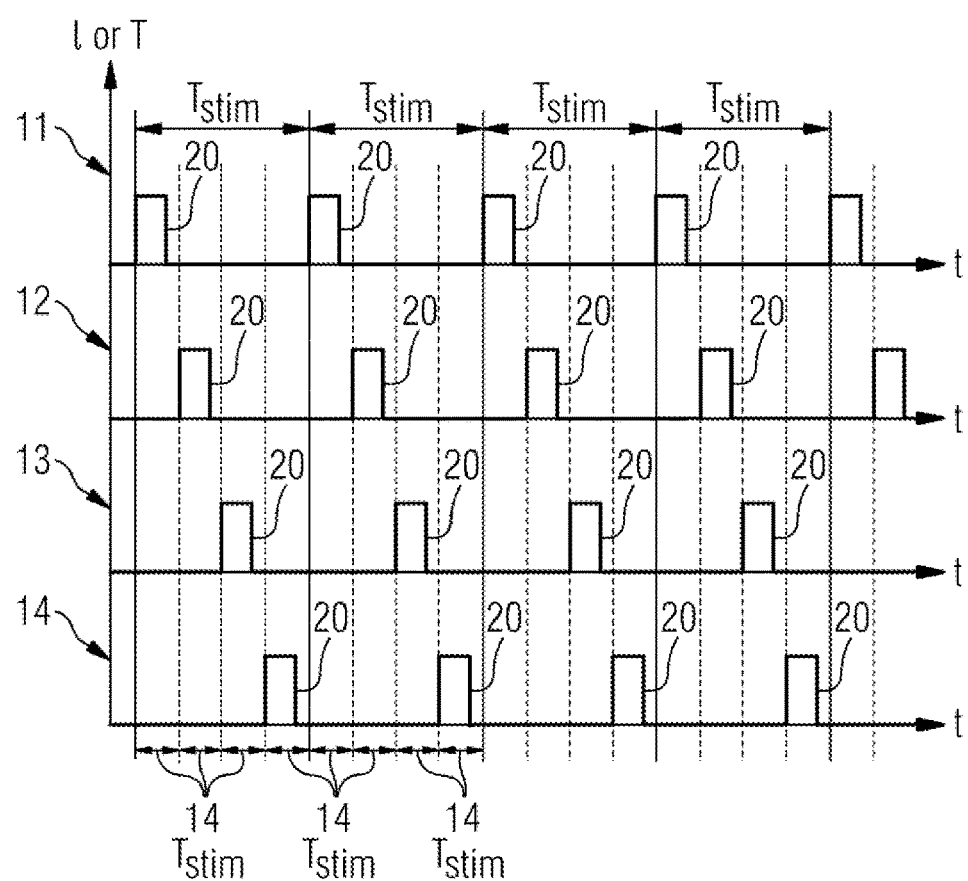
FIGS. 7 to 9 illustrate schematic representations of stimulation methods carried out using the apparatus 100.

A stimulation method suitable for the above-described purposes is shown schematically in FIG. 7. The stimuli 20 applied via the stimulation units 11 to 14 are shown beneath one another over the time t in FIG. 7. The vibration stimuli, tactile stimuli and thermal stimuli shown in FIGS. 3A to 5C can be used as stimuli 20, for example. The diagram shown in FIG. 7 is divided into periodically repeating first time periods of the length $T_{stim}$. The frequency $f_{stim}=1/T_{stim}$ at which the first time periods of the length $T_{stim}$ are repeated can lie in the range from 1 to 60 Hz and in particular in the range from 30 to 60 Hz or in the range from 1 to 30 Hz or in the range from 1 to 20 Hz or in the range from 5 to 20 Hz, but can also have lower or higher values.

The first time periods of the length $T_{stim}$ are further more divided into two time periods of the length $T_{stim}/4$. On a stimulation via N stimulation units, the first time periods could be divided into N second time periods of the length $T_{stim}/N$.

In accordance with an embodiment, each of the stimulation units 11 to 14 generates no more than one stimulus 20 within a first time period. Stimuli 20 from different stimulation units 11 to 14 can be generated in second time periods following one another.

In the embodiment shown in FIG. 7, each of the stimulation units 11 to 14 applies a stimulus 20 strictly periodically at the frequency $f_{stim}$. The administration of the stimuli 20 via different stimulation units 11 to 14 takes place with a time delay between the individual stimulation units 11 to 14 by $T_{stim}/4$.

In the case of N stimulation time units, the time delay between two respective mutually following stimuli 20 can lie, for example, in the range of an Nth of the period $1/f_{stim}$, i.e. $1/(N \times f_{stim})=T_{stim}/N$, i.e. in particular the time $T_{stim}/N$ elapses between the start times of two mutually following stimuli 20.

The frequency $F_{stim}$ can lie, for example, in the range of the mean frequency of the pathologically rhythmic activity of the target network. With diseases in which an increased neuronal synchronization is present, the mean frequency typically lies in the range from 1 to 30 Hz, but can also lie outside this range. It must be noted in this respect that the frequency at which the affected neurons fire synchronously is usually not constant, but can rather certainly have variations and furthermore shows individual deviations in each patient.

Deviations from the strictly periodic stimulation patterns shown in FIG. 7 can take place in different manners. For example, the time delay $T_{stim}$ between mutually following stimuli 20 generated by the same stimulation unit cannot always be of equal magnitude, but can rather vary in the range of ±10% or ±5% or ±3% around $T_{stim}$. Furthermore, the time interval between two mutually following stimuli 20 generated by different stimulation units can also vary in the range of ±10% or ±5% or ±3% around $T_{stim}/N$. Provision can by all means be made that the time intervals between the individual stimuli 20 are selected as different. Furthermore, the delay times can also be varied during the treatment of a patient. The delay times can also be adjusted with reference to the physiological signal transit times.

Furthermore, pauses can be provided during the application of the stimuli 20 during which no stimulation occurs. Such a pause is shown by way of example in FIG. 8. The pauses can be selected to be of any desired length and can in particular amount to a whole-number multiple of the period $T_{stim}$. Furthermore, the pauses can also be observed after any desired number of stimulations. E.g. a stimulation can be carried out during n mutually following periods of the length $T_{stim}$ and subsequently a pause can be observed during m periods of the length $T_{stim}$, without stimulation, where n and m are small whole numbers, e.g. in the range from 1 to 10. This scheme can either be continued or modified periodically or stochastically and/or deterministically or in mixed stochastic/deterministic form.

A further possibility to deviate from the strictly periodic stimulation pattern shown in FIG. 7 comprises varying the time sequence of the individual stimuli 20 stochastically or deterministically or in mixed stochastic/deterministic form.

Figure 9:
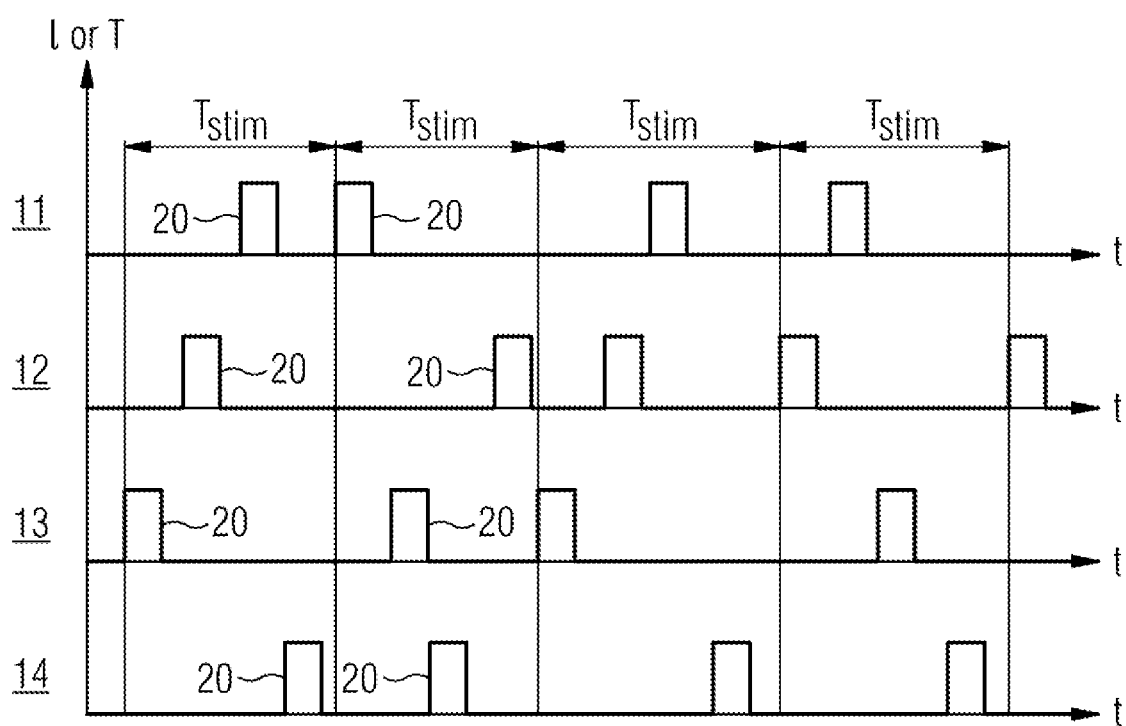

Furthermore, the order in which the stimulation units 11 to 14 apply the stimuli 20 can be varied per period Tstim(or also in other time steps), as is shown by way of example in FIG. 9. This randomization can take place stochastically or deterministically or in a mixed stochastic/deterministic manner.

Figure 8:
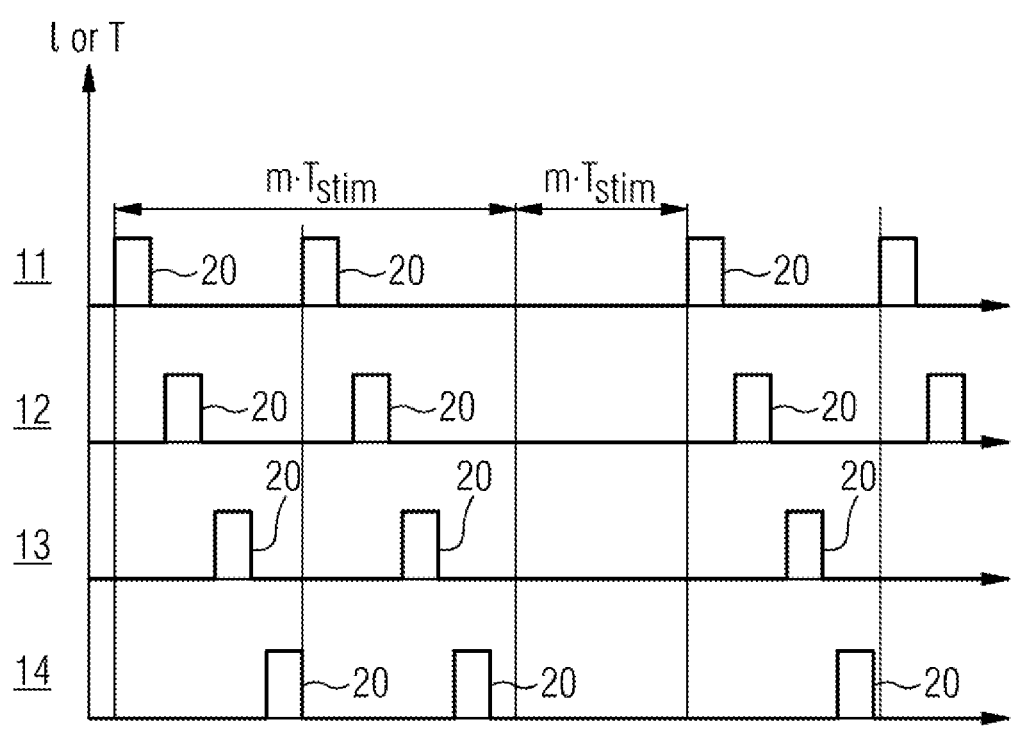

The randomization shown in FIG. 9 can be combined with the stimulation form shown in FIG. 8. For example, a repeat randomization can be carried out in each of the n mutually following stimulation time periods of the length $T_{stim}$, or a randomization takes place after each pause of the lengths $m \times T_{stim}$ and the order in which the stimulation units 11 to 14 apply the stimuli 20 remains constant within the n following stimulation time periods.

Furthermore, only a specific number of stimulation units 11 to 14 can be used for the stimulation per period $T_{stim}$ (or in another time interval) and the stimulation units participating in the stimulation can be varied in each time interval. This variation can also take place stochastically or deterministically or in a mixed stochastic/deterministic manner.

It is conceivable that the stimulation is started by the patient, for example by a telemetric activation. In this case, the patient can e.g. activate the stimulation for a predetermined time period of e.g. 60 minutes by means of an external transmitter or the patient can start and end the stimulation independently.

Figure 10:
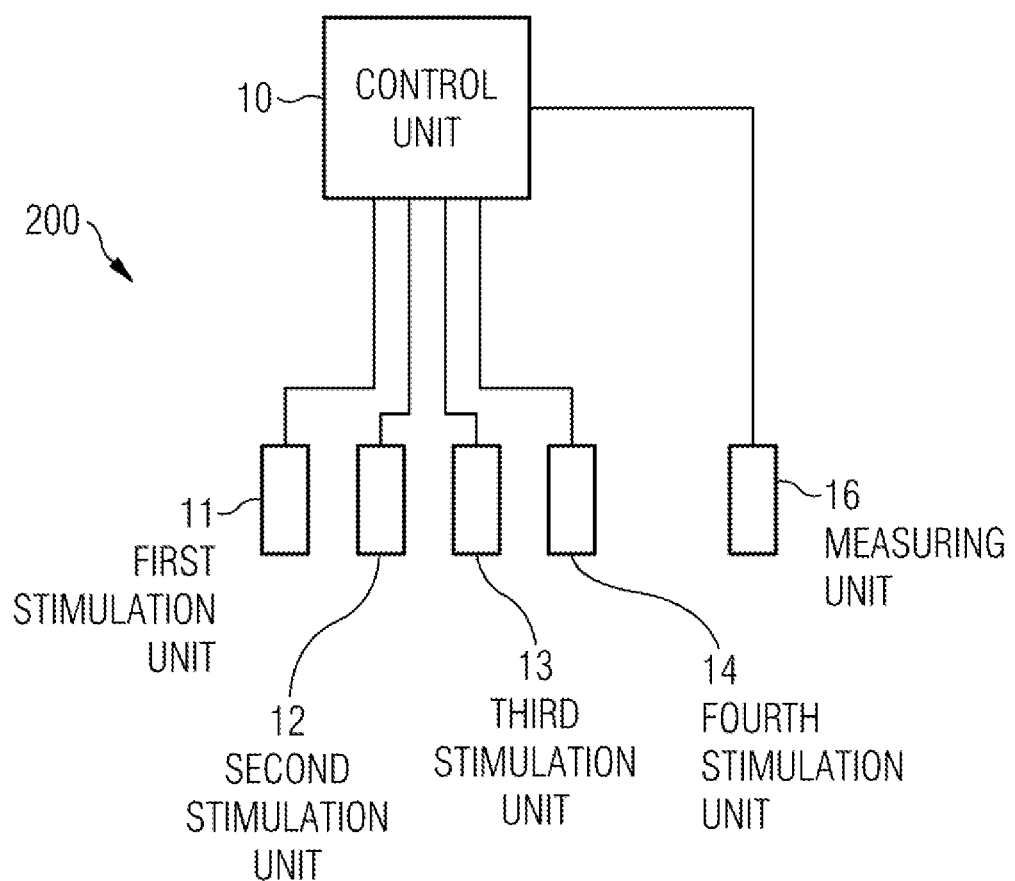
FIG. 10 illustrates a schematic representation of an apparatus 200 for generating vibration stimuli, tactile stimuli and/or thermal stimuli in accordance with a further embodiment.

The apparatus 100 can be operated, for example, in a so-called open loop mode in which the control unit 10 controls the stimulation units 11 to 14 such that they generate predefined stimuli 20 which are output to the skin tissue. Furthermore, the apparatus 100 can also be further developed into an apparatus 200 shown in FIG. 10 which represents a so-called closed-loop system. The apparatus 200 additionally includes a measuring unit 16 which provides one or more measured signal taken at the patient and forwards them to the control unit 10. Provision can be made that the control unit 10 controls the stimulation units 11 to 14 using the measured signals taken by the measuring unit 16.

The measuring unit 16 can be non-invasive sensors such as electroencephalography (EEG) electrodes, magnetoencephalography (MEG) sensors, accelerometers, electromyography (EMG) electrodes and sensors for determining blood pressure, respiration or electric resistance of the skin. The measuring unit 16 can furthermore be implanted in the body of the patient in the form of one or more sensors. Deep-brain electrodes, subdural or epidural brain electrodes, subcutaneous EEG electrodes and subdural or epidural spinal cord electrodes can serve as invasive sensors, for example. Furthermore, electrodes to be fastened to peripheral nerves can be used as sensors. The neuronal activity in the stimulated target area, i.e. e.g. the neuronal activity of the neuronal population 30 shown schematically in FIG. 6 or an area associated therewith can in particular be measured by means of the measuring unit 16.

Different embodiments are conceivable with respect to the cooperation of the control unit 10 with the measuring unit 16. A demand activated stimulation can be carried out by the control unit 10, for example. For this purpose, the control unit 10 detects the presence and/or the characteristic of one or more pathological features using the measured signals taken by the measuring unit 16. The amplitude or the amount of the neuronal activity can, for example, be measured and compared with a predefined threshold value. The control unit 10 can be designed so that a stimulation is started as soon as the predefined threshold value is exceeded. Alternatively to the controlling of the times of the stimulation using the measured signals taken by the measuring unit 16 or in addition thereto, the strength of the stimuli can be set by the control unit 10 using the characterization of the pathological features. E.g. one or more threshold values can be predefined and, on an exceeding of the amplitude or of the amount of the measured signals above a specific threshold, the control unit 10 sets a specific strength of the stimuli 20, e.g. a specific frequency $f_{vib}$ or impression depth 12 in the case of vibration stimuli.

Furthermore, provision can be made that the measured signals taken by the measuring unit 16 are used as stimuli 20 directly or, optionally, after one or more processing steps, and are fed by the control unit 1 into one or more of the stimulation units 11 to 14. For example, the measured signals can be amplified and processed, optionally after mathematical offsetting (e.g. after mixing the measured signals) with a time delay and linear and/or non-linear offset steps and combinations and can be fed into at least one of the stimulation unit 11 to 14. The offset mode is selected in this respect so that the pathological neuronal activity is countered and the stimulation signal likewise disappears or is at least considerably reduced in its strength as the pathological neuronal activity reduces. The (possibly forwarded) measured signals can, for example, be applied analogously to the stimulation process in accordance with FIG. 7 with a time delay of $T_{stim}/4$ via the individual stimulation units 11 to 14.

This type of stimulation in which the measured signals taken at the patient are fed back into the body of the patient for the dresynchronization of a neuronal population could generally also be carried out using only one single stimulation unit; however, any desired larger number of stimulation units can also be provided.

The measured signals can, for example be amplified for generating the stimuli 20 and can be used, optionally after mathematical offsetting (e.g. after mixing the measured signals) with a time delay and linear and/or non-linear offset steps, for the electric control of the stimulation units which then convert the measured signals into vibration stimuli, tactile stimuli or thermal stimuli. The offset mode can in this respect be selected so that the pathological neuronal activity is countered and the applied stimulus likewise disappears or is at least considerably reduced in its strength as the neuronal activity decreases.

In the following, linear and non-linear processing steps will be described with which measured signals acquired with the aid of the measuring unit 16 can be processed before they are used for controlling the stimulation units. On a non-linear processing of the measured signals, the phase of the neuronal activity in the respective stimulated subpopulations is not reset, but rather the synchronization in the pathologically active neuronal population is suppressed in that the saturation process of the synchronization is influenced.

On a linear processing of a measured signal acquired by the measuring unit 16, the measured signal can, for example, be filtered and/or amplified and/or acted on by a time delay before the signal processed in this manner is fed into the stimulation unit and is converted into a vibration stimulus and/or tactile stimulus and/or thermal stimulus. It is assumed as an example that the measured signal had been taken by means of an EEG electrode and represents the pathological activity in the target area. Accordingly, the measured signal is a sine oscillation with a frequency in the range from 1 to 30 Hz. It is furthermore assumed by way of example that the measured signal has a frequency of 5 Hz. The measured signal can be filtered by means of a bandpass filter having a transmission range in the range of 5 Hz and can be amplified by means of an amplifier so that it has a level suitable for the control of the stimulation unit. Subsequently, the amplified sine oscillation thus obtained is used for controlling the stimulation unit. In the case of a stimulation unit for applying vibration stimuli or tactile stimuli, the stimulation element then carries out a sinusoidal movement at a frequency of 5 Hz.

Provided that a number N of stimulation units is used for the stimulation, the measured signal can be acted on by the time delays $T_{stim}/N$ shown in FIG. 7 before it is fed into the corresponding stimulation units.

In the following, it will be explained with reference to an example how a measured signal acquired by the measuring unit 16 can be subjected to a non-linear processing before it is used as a stimulation stimulus. Exactly as in the linear processing, the measured signal can also be filtered and/or amplified and/or acted on by a time delay here.

The starting point is an equation for the stimulation stimulus S(t):

$$s(t) = K \cdot \overline{Z}^2(t) \cdot \overline{Z}^*(t-\tau) \quad (2)$$

In equation (2), K is an amplification fact which can be selected suitably and $\overline{Z}(t)$ is a mean state variable of the measured signal. $\overline{Z}(t)$ is a complex variable and can be represented as follows:

$$\overline{Z}(t) = X(t) + iY(t), \quad (3)$$

where X(t) can e.g. correspond to the neurological measured signal and i is the imaginary unit. Since the observed frequencies lie in the range from 10 Hz=1/100 ms=$1/T_\alpha$, the imaginary part Y(t) can be approximated by $(X(t-\tau_\alpha))$, where $\tau_\alpha = T_\alpha/4$ applies, for example. There thus results:

$$s(t) = K \cdot [x(t) + iX(t-\tau_\alpha)]^2 \cdot [X(t-\tau) - iX(t-\tau-\tau_\alpha)] \quad (4)$$

Equation (4) can be transformed as follows:

$$s(t) = K \cdot [X(t)^2 \cdot X(t-\tau) + i2X(t) \cdot X(t-\tau_\alpha) \cdot X(t-\tau) - X(t-\tau_\alpha) \cdot X(t-\tau) - iX(t-\tau-\tau_\alpha) \cdot X(t)^2 + 2X(t) \cdot X(t-\tau_\alpha) \cdot X(t-\tau-\tau_\alpha) + iX(t-\tau-\tau_\alpha) \cdot X(t-\tau_\alpha)] \quad (5)$$

The real part from equation (5) is used as the stimulation stimulus:

$$\text{real}[s(t)] = K \cdot [X(t)^2 \cdot X(t-\tau) - X(t-\tau_\alpha) \cdot X(t-\tau) + 2X(t) \cdot X(t-\tau_\alpha) \cdot X(t-\tau-\tau_\alpha)] \quad (6)$$

Figure 11A:
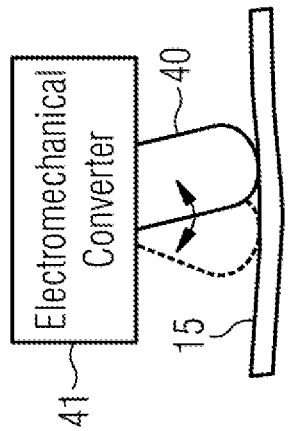
FIG. 11A to 13C illustrate schematic representations of stimulation units for generating vibration stimuli and/or tactile stimuli.
Figure 11B:
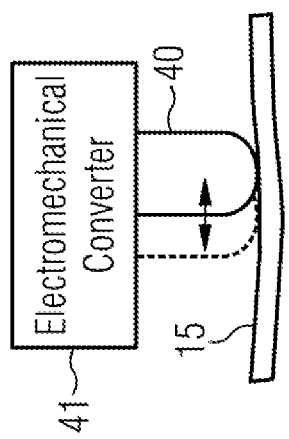
Figure 11C:
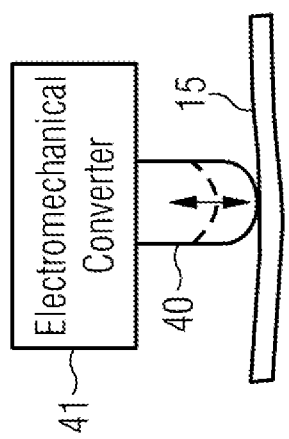

FIGS. 11A to 11C schematically show different possibilities for realizing a stimulation unit for generating vibration stimuli and/or tactile stimuli such as are shown in FIGS. 3A to 4. The stimulation units include a stimulation element 40, for example in the form of a bar, with whose one end the skin 15 of the patient is stimulated. The stimulation element 40 is driven by an electromechanical converter 41 (or actor or actuator) which converts electric energy into a movement of the stimulation element 40. DC motors, voice coils, piezoelectric converters or converters comprising electroactive polymers (EAPs) which change their form on application of an electric voltage are suitable as electromechanical converters 41.

The electromechanical converters 41 can be designed so that the stimulation element 40 is deflected perpendicular to the skin's surface (cf.

FIG. 11A) or in parallel thereto (cf. FIG. 11B). The movement of the stimulation element 40 can, however, also take place on any other desired paths. A pendular deflection of the stimulation element 40 is shown as an example of this in FIG. 11C.

Figure 12A:
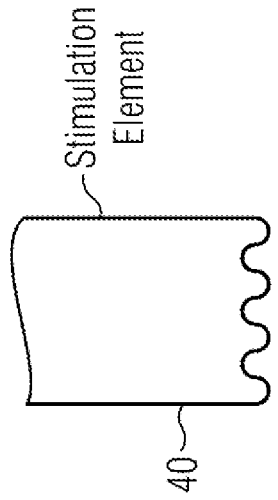
Figure 12B:
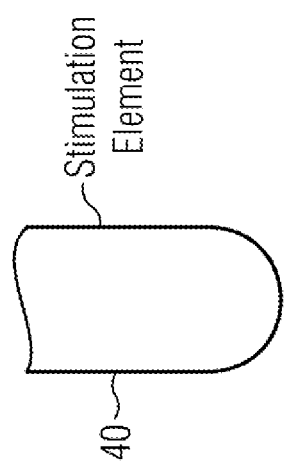

The end of the stimulation element 40 that comes into contact with the skin's surface and ultimately generates the stimuli can. for example, substantially have the shape of a hemisphere (cf. FIG. 12A) or can have a nub-like surface (cf. FIG. 12B) or can have another suitable shape.

Figure 13A:
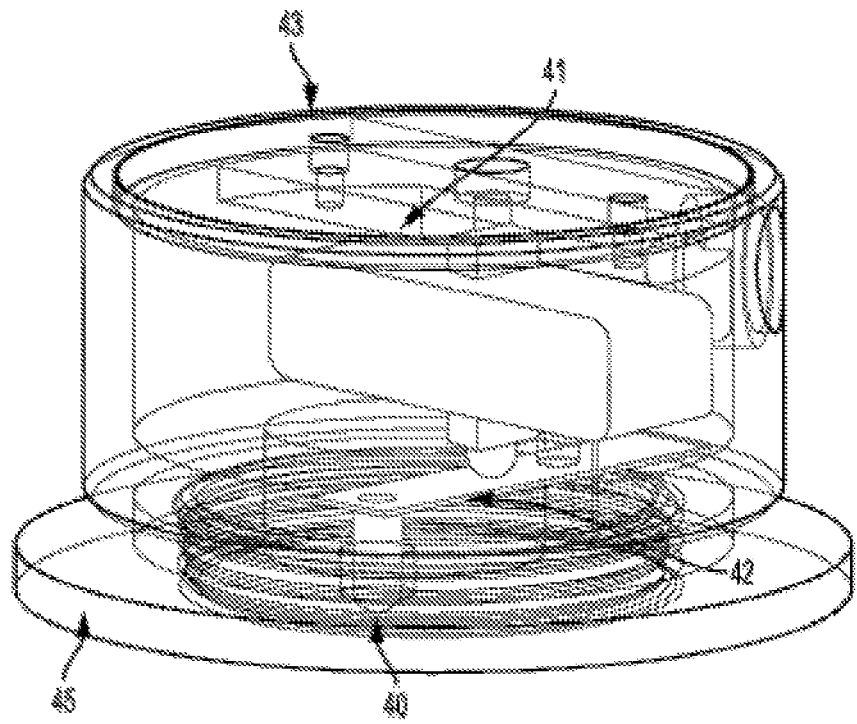
Figure 13B:
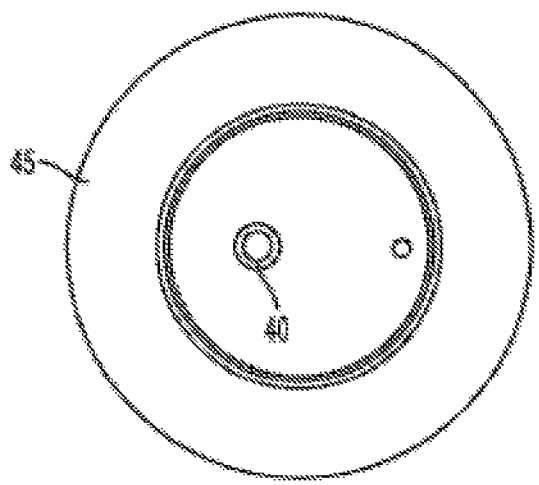
Figure 13C:
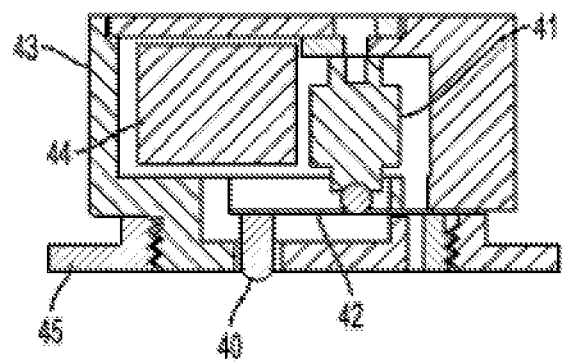

An embodiment of a stimulation element for applying vibration stimuli and/or tactile stimuli is shown in FIGS. 13A to 13C in phantom view (cf. FIG. 13A), in plan view from below (cf. FIG. 13B) and in cross-section (cf. FIG. 13C). The present stimulation element includes a piezoactuator 41 as an electromechanical converter. Since the deflection of the piezoactuator 41 is not sufficient for the intended purposes, a mechanism can be provided for amplifying the deflection of the piezoactuator 41. A lever arm 42 is shown by way of example here which amplifies the movement of the piezoactuator 41. The lever arm is here an elongate flexible spring 42 whose one end is fastened to the housing 43 of the stimulation element and to whose other end the stimulation element 40 is attached. The piezoactuator 41 presses onto the upper side of the flexible spring 42 and the stimulation element 40 attached to the lower side of the flexible spring 42 follows the deflection of the piezoactuator 41 with an amplitude amplified due to the geometrical arrangement and applies the vibration stimuli and/or tactile stimuli to the skin of the patient. The lower side of the stimulation element 40 which comes into contact with the skin can have different geometries and dimensions. The stimulation element 40 can be flat, round or irregular at its lower side, for example.

Furthermore a space 44 for electronics and connection terminals can be provided in the housing 43 of the stimulation element which accommodates the piezoactuator 41 and the amplification mechanism. In addition, an adjustment ring 45 is attached to the lower side of the housing 43; it is connected to the housing 43 via a thread and allows an adjustment of the height by which the stimulation element 40 projects from the lower side of the stimulation unit in its position of rest. During operation, the lower side of the stimulation unit is seated on the skin of the patient and is fastened to the body of the patient by a suitable cuff, for example. In addition to or alternatively to the cuff, the stimulation unit could be fastened to the skin of the patient by a single-sided or double-sided medical adhesive tape. The housing 43 protects the patient from possible risks such as electric voltage.

Figure 14A:
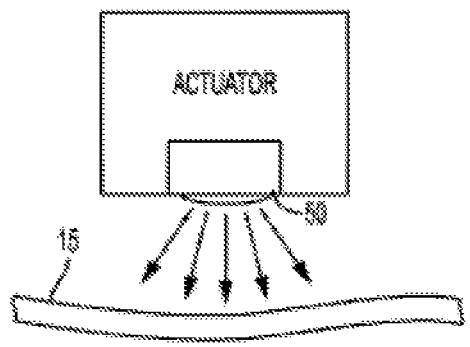
FIG. 14A to 15C illustrate schematic representations of stimulation units for generating thermal stimuli.
Figure 14B:
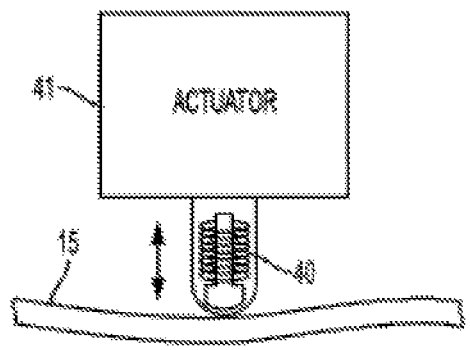

FIG. 14A to 14B schematically show differently designed stimulation units for generating thermal stimuli such as are shown in FIGS. 5A to 5C. The stimulation unit shown in FIG. 14A works contactlessly and effects a heating of the skin by the light of an infrared LED 50.

Figure 14C:
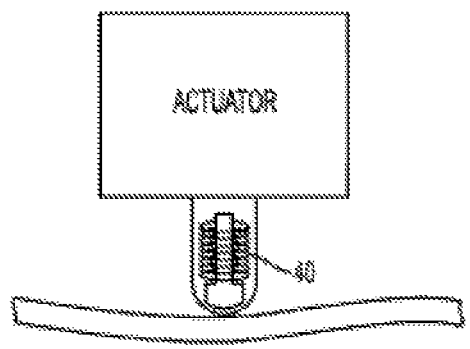

Stimulation units which apply thermal stimuli by contact with the skin's surface are shown in FIGS. 14B and 14C. The stimulation unit shown in FIG. 14B includes substantially the same components as the stimulation unit from FIG. 11A with an electromechanical converter 41 and a bar-shaped stimulation element 40. The stimulation unit of FIG. 14B additionally has a heating element and/or cooling element (e.g. in the form of a heating loop) which heats or cools the stimulation element. The thermal stimuli are generated by the movements of the stimulation element 40 with which the stimulation element 40 repeatedly comes into contact with the skin 15 and is removed again. The temperature of the stimulation element 40 can be constant during the total stimulation.

Alternatively, the heatable or coolable stimulation element 40 can, as shown in FIG. 14C, be in contact with the skin 15 of the patient during the total stimulation period. The thermal stimuli are in this case generated by a time variation of the temperature of the stimulation element 40. An electromechanical converter is not necessarily required in this embodiment.

Figure 15A:
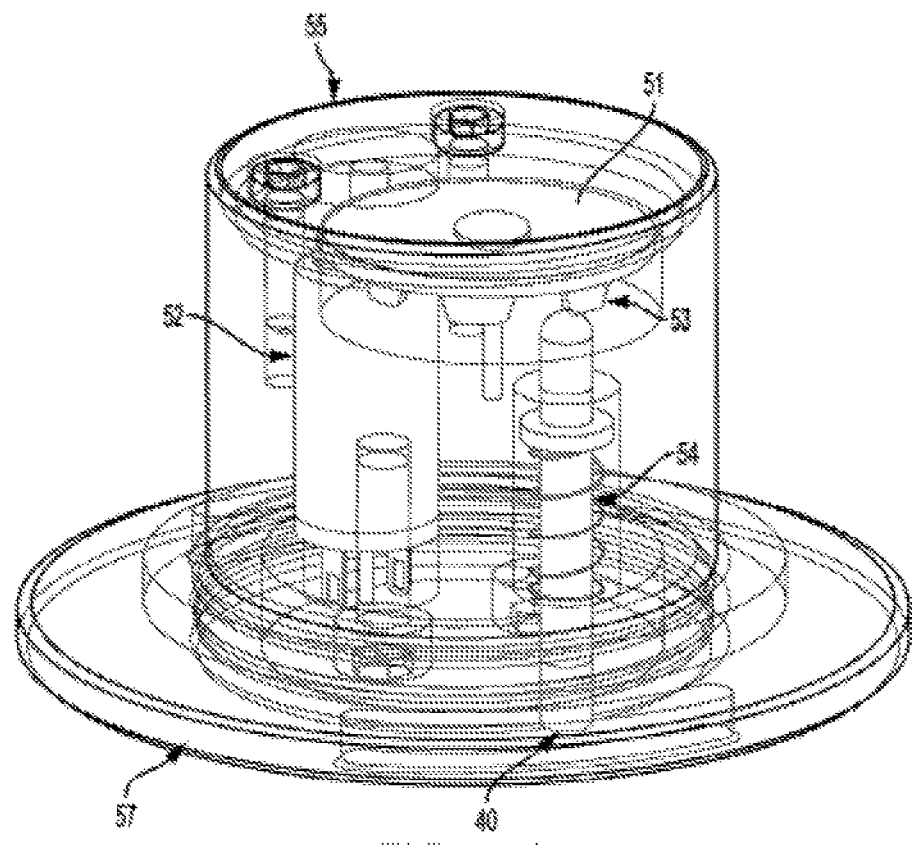
Figure 15B:
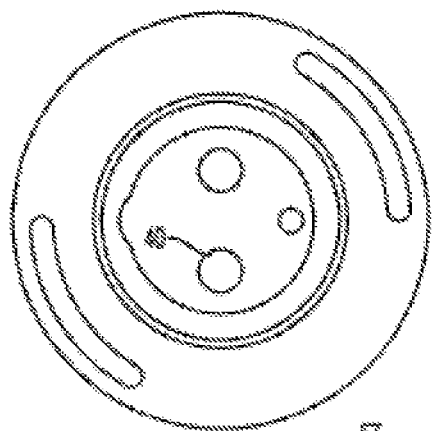
Figure 15C:
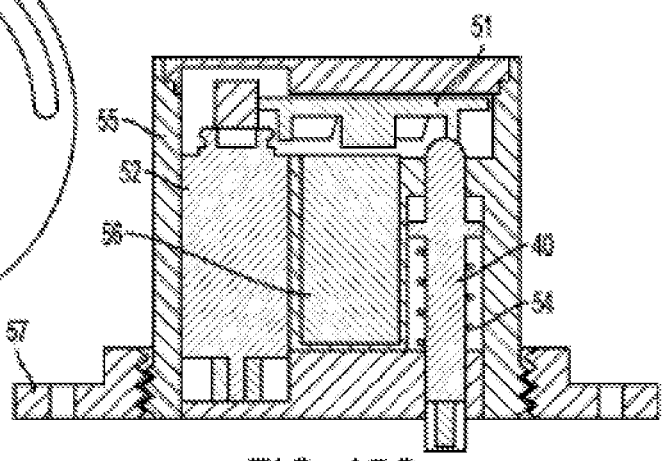

An embodiment of a stimulation element for applying thermal stimuli is shown in FIGS. 15A to 15C in phantom view (cf. FIG. 15A), in plan view from below (cf. FIG. 15B) and in cross-section (cf. FIG. 15C). The stimulation unit includes a bar-shaped stimulation element 40 whose lower end is heatable and/or coolable. The stimulation element 40 is driven by a cam disk 51 at its upper end. A DC motor 52 sets the cam disk 51 into rotation during the stimulation. The stimulation element 40 is deflected downwardly by the cams 53 attached to the lower side of the cam disk 51. A restoration spring 54 provides that the stimulation element 40 subsequently returns to its starting position. The rotational movement of the cam disk 51 is converted into a linear movement of the stimulation element 40 by this mechanism. As described above, the stimulation element 40 can either be in contact with the skin of the patient for a specific time or the stimulation element 40 is brought cyclically onto the skin by a rotation of the cam disk 51 and is removed again.

The components of the stimulation unit can be introduced into a housing 55. A space 56 for electronics and connection terminals can be provided in the housing 55. In addition, an adjustment ring 57 can be attached to the lower side of the housing 55; it is connected to the housing 55 via a thread and allows an adjustment of the height by which the stimulation element 40 projects from the lower side of the stimulation unit in its position of rest (the stimulation element 40 can also lie completely above the lower side of the adjustment ring in its position of rest due to the adjustment ring). During operation, the lower side of the stimulation unit is seated on the skin of the patient and is fastened to the body of the patient by a suitable cuff, for example. In addition to or alternatively to the cuff, the stimulation unit could be fastened to the skin of the patient by a single-sided or double-sided medical adhesive tape. The housing 55 protects the patient from possible risks such as electric voltage.

Figure 16:
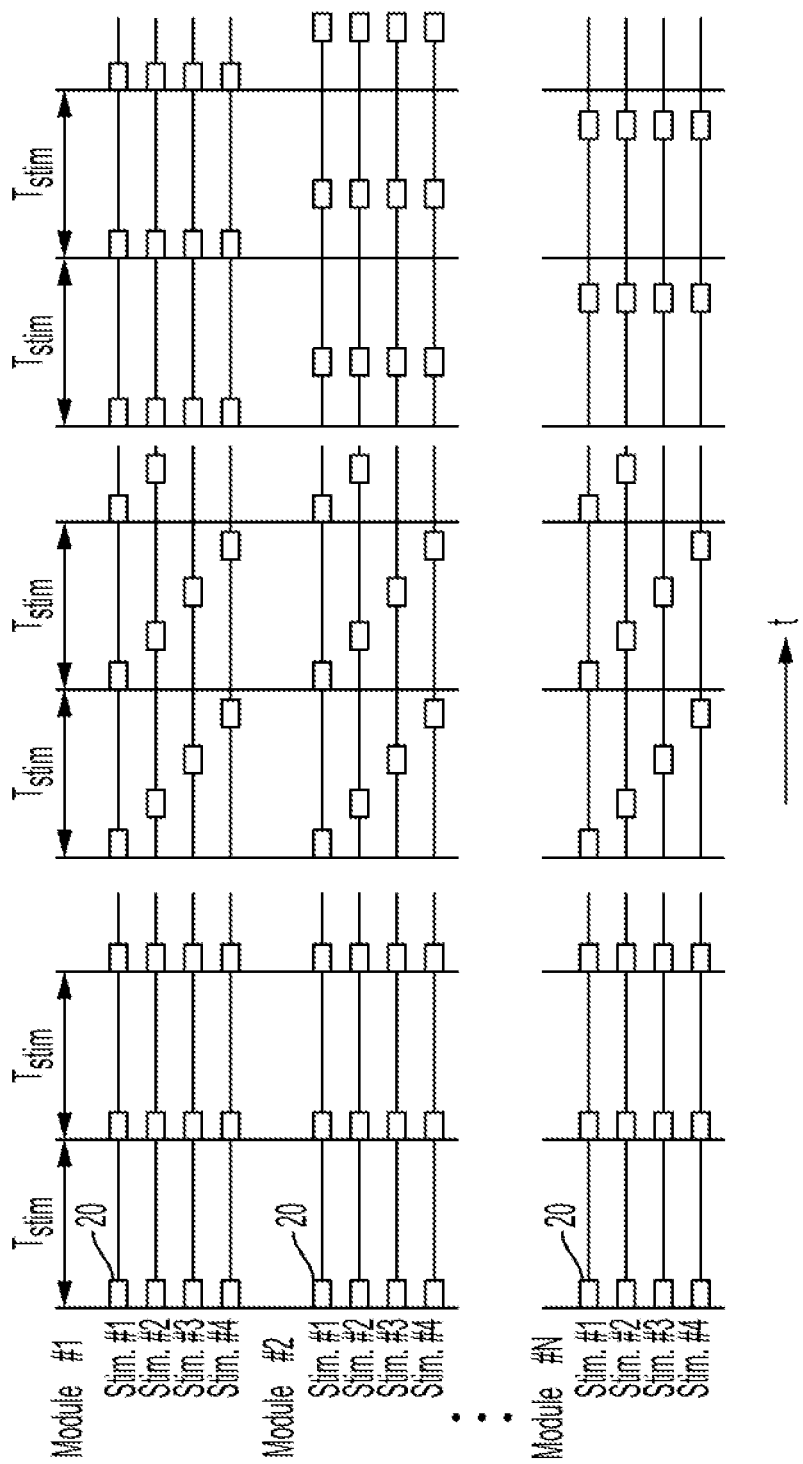
FIGS. 16 and 17 illustrate schematic representations of stimulation methods.

The stimulation units described in this application can be fastened individually to patients or several can also be integrated in one module. For example, a module can include a cuff with a plurality of stimulation units fastened thereto. The cuff can then be fastened to an arm or leg of the patient. FIG. 16 shows stimulation methods such as can be carried out using a total of N modules which each include four stimulation units, for example. In the stimulation method shown at the far left in FIG. 16, all the stimulation units apply a vibration stimuli 20, tactile stimuli 20 or thermal stimulus 20 at the start of a stimulation period $T_{stim}$. In the stimulation method shown in the middle of FIG. 16, the stimuli 20 of the four different stimulation units of a module are each mutually displaced by $T_{stim}/4$. In this case, exactly one stimulation unit of each module applies a stimulus 20 in each time period of the length $T_{stim}/4$. In the stimulation method shown at the far right in FIG. 16, the four stimulation units of a module generate their stimuli 20 simultaneously, but the stimuli 20 of different modules are mutually displaced.

In all the stimulation methods shown in FIG. 16, any desired pauses can also be observed during the stimulation. Typically, the stimulation pauses have the length of one or more stimulation periods $T_{stim}$. This is shown by way of example in FIG. 17. In the stimulation method shown there, a stimulation is carried out during two mutually following stimulation periods $T_{stim}$; then a stimulation pause is observed during a stimulation period $T_{stim}$. This pattern repeats periodically.

Figure 17:
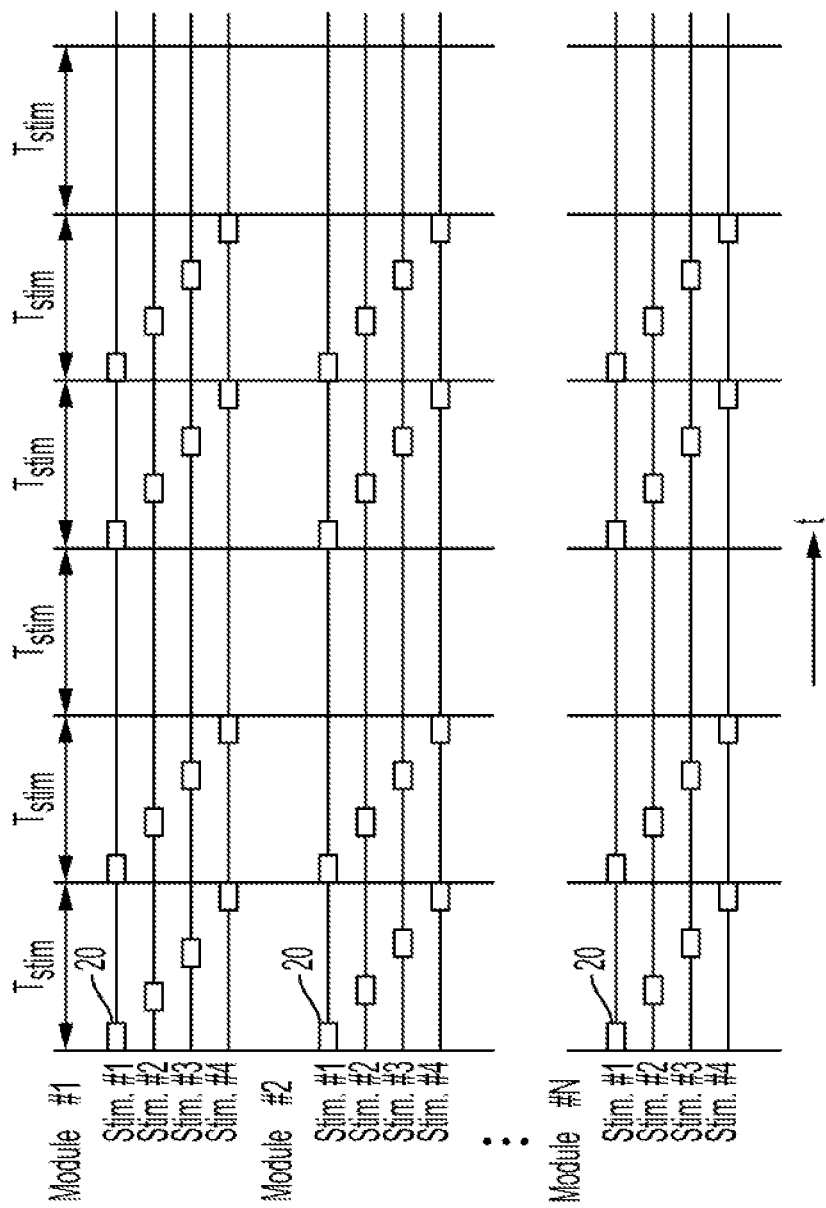

Furthermore, a randomization of the order in which the individual stimulation units generate stimuli can be added to the stimulation methods shown in FIGS. 16 and 17, with the following randomizations being conceivable among others:

1. Randomization of the stimulus sequences for each stimulation period Tstim coherently over all modules, i.e. at the start of each stimulation period Tstim, an order is fixed in which the stimulation units generate the stimuli (e.g. the order Stim. #4, Stim. #2, Stim. #3, Stim. #1) and this order applies to all modules.
2. Randomization of the stimulus sequences for a block of mutually following stimulation periods Tsar, coherently over all modules, i.e. at the start of e block of mutually following stimulation periods Tstim shown in FIG. 17 (or after a stimulation pause), an order is fixed in which the stimulation units generate the stimuli (e.g. the order Stim. #4, Slim. #2, Stim. #3, Stim. #1) and this order applies to all modules for the stimulation block up to the next pause.
3. Randomization of the stimulus sequences not varied coherently over all modules, but rather only coherently over a subgroup of all modules, i.e. a randomization in accordance with the above Items 1. or 2. is only carried out for a specific module (e.g. the module #2); the remaining modules behave as shown in FIG. 16.
4. Randomization of the stimulus sequences not varied coherently over all modules, but rather only coherently over a subgroup of all modules, i.e. a randomization in accordance with the above Items 1. or 2. is only carried out for two or more modules (e.g. the modules #2and #4); the remaining modules behave as shown in FIG. 16.
5. Randomization of the stimulus sequences in uncorrelated form between different modules, i.e. an order in which the stimulation units generate the stimuli is fixed for each module independently of the other modules for each stimulation period $T_{stim}$, or for each block of mutually following stimulation periods $T_{stim}$ between two pauses.

Figure 18:
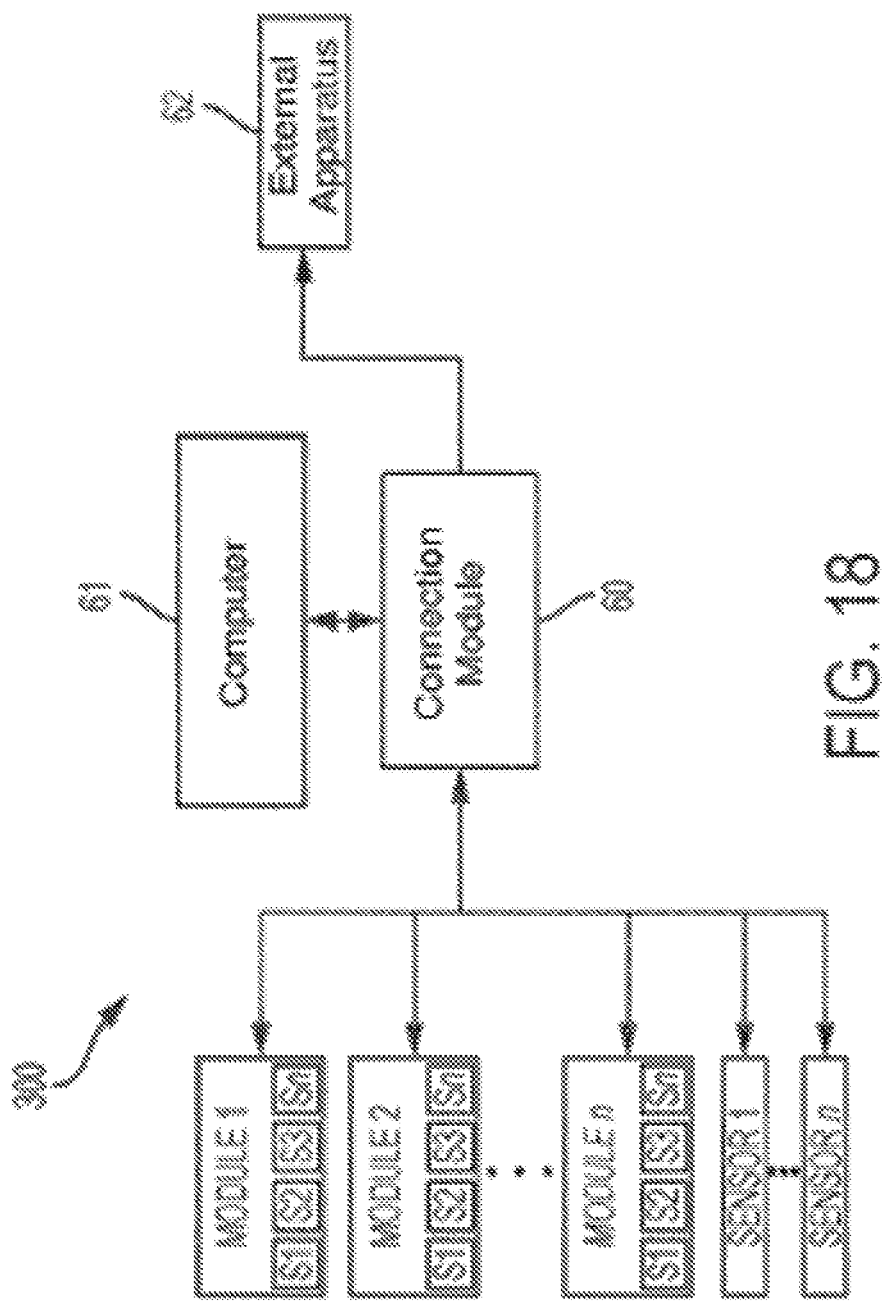

The block diagram of an apparatus 300 for generating vibration stimuli and/or tactile stimuli and/or thermal stimuli is shown schematically in FIG. 18. The apparatus 300 includes n modules each having n stimulation units and n sensors. The modules and sensors are connected via connection lines or via radio (e.g. via a WPAN (wireless personal area network) network) to a connection module 60 which can in turn be connected to a computer 62 e.g. to a-+ laptop, and to external apparatus 62. All modules and sensors do not necessarily have to be used simultaneously; depending on the type of stimulation, only a subset thereof can also be used. The modules and/or sensors can be supplied with power by batteries or rechargeable batteries so that they are independent of a central power supply. The user, for example a physician, can select a stimulation method by means of suitable software stored on the computer 61 and can set the parameters of this stimulation method.

The control of the stimulation units integrated in the modules can take place via the computer 61. As an alternative, a control unit 10 can be integrated in each module (cf. FIG. 19A) and is responsible for the control of the stimulation units of the respective module. This allows a largely independent operation of the modules. Furthermore, a separate control unit 10 can be provided for each stimulation unit (cf. FIG. 19B). This allows the greatest variety in the operation of the stimulation units, but the weight and the dimensions of the modules are hereby increased in size. As a further alternative, the control unit 10 can be positioned centrally in the connection module 60. The low weight and small size of the modules and an inexpensive manufacture are advantageous therein. However, in this embodiment, the modules cannot be operated independently of the connection module 60.

What is claimed:

1. A method for treating a patient with a disease in which there is an increased neuronal synchronization of neuronal activity of a population of neurons of the patient, the method comprising:

generating, by a first stimulation unit, first stimuli to skin of the patient that, upon being received by receptors disposed in or beneath the skin of the patient and transmitted to a first sub-population of the population of neurons, effect a reset of a phase of neuronal activity of the first sub-population;

generating, by a second stimulation unit, second stimuli to the skin of the patient that, upon being received by receptors disposed in or beneath the skin of the patient and transmitted to a second sub-population of the population of neurons, effect a reset of a phase of neuronal activity of the second sub-population, wherein the first and second stimuli are at least one of vibratory stimuli, tactile stimuli and thermal stimuli, wherein the generating of the first and second stimuli are performed to apply the first and second stimuli to the skin of the patient at different target regions and least partially different times such that the phase of the neuronal activity of the first and the second sub-population are reset at different times and such that the first and the second sub-population have different phases of neuronal activity by controlling each of the first stimulation unit and the second stimulation unit to generate the stimuli during periodic stimulation time periods, and wherein the generating, by the first stimulation unit and the second stimulation unit, generates at most one of the stimuli during each stimulation time period of the stimulation time periods and, among the periodic stimulation time periods, an order in which the first stimulation unit and the second stimulation unit generate the respective stimuli per stimulation period is varied.

2. The method according to claim 1, wherein the first and second stimuli are respectively repeated on average at a frequency of 1 to 60 Hz during a stimulation period.

3. The method in accordance with claim 1, wherein the varying of the order in which the first and second stimulation units generate the respective stimuli per stimulation period is according to a stochastic manner, a deterministic manner or a mixed stochastic and deterministic manner.

4. The method in accordance with claim 1, wherein the first and second stimulation units are part of a plurality of stimulation units and comprises between two and twelve stimulation units.

5. The method in accordance with claim 1, further comprising generating a pause between two subsequent stimulation time periods during which no stimulation by the first and second stimulation units occurs.

6. The method in accordance with claim 1, further comprising performing a stimulation according to a scheme comprising a number of n mutually following stimulation time periods and subsequently a pause period during which no stimulation by the first and second stimulation units occurs, wherein n is a whole number in a range from 1 to 10.

7. The method in accordance with claim 6, further comprising continuing or modifying the scheme periodically or stochastically or deterministically or in mixed stochastic and deterministic manner.

8. The method in accordance with claim 6, further comprising modifying the scheme periodically by adapting at least one of the number n of mutually following stimulation time periods and a length of the pause period.

9. The method in accordance with claim 6, further comprising varying the order in which the first and second stimulation units generates the respective stimuli per stimulation period among at least one of the n mutually following stimulation time periods or among mutually following schemes.

10. The method in accordance with claim 1, wherein the first and second stimulation units are part of a plurality of stimulation units, and wherein the method further comprises selecting per stimulation time period a number and selection of stimulation units of the plurality of stimulation units participating in the stimulation, wherein at least one of the number and selection of the stimulation units participating in the stimulation varies among the stimulation time periods.

11. The method in accordance with claim 1, further comprising measuring pathological features experienced by the patient with the disease in response to the generated stimuli and adjusting the stimuli based on the measured pathological features.

\* \* \* \* \*